US006256541B1

(12) United States Patent
Heil et al.

(10) Patent No.: US 6,256,541 B1
(45) Date of Patent: *Jul. 3, 2001

(54) ENDOCARDIAL LEAD HAVING DEFIBRILLATION AND SENSING ELECTRODES WITH SEPTAL ANCHORING

(75) Inventors: John E. Heil, White Bear Lake; Ronald W. Heil, Jr., Roseville; Avram Scheiner, Vadnais Heights; Yayun Lin, St. Paul; Lyle A. Bye, Lino Lakes, all of MN (US); J. John Lattuca, Weybridge (GB)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/062,268

(22) Filed: Apr. 17, 1998

(51) Int. Cl.[7] .................................................. A61N 1/05
(52) U.S. Cl. ......................... 607/123; 607/122; 607/126; 607/127; 607/128; 607/5
(58) Field of Search .................................. 607/122, 123, 607/126, 127, 128, 5

(56) References Cited

U.S. PATENT DOCUMENTS

| 4,154,247 | 5/1979 | O'Neill | 128/419 P |
|---|---|---|---|
| 4,289,144 | 9/1981 | Gilman | 128/785 |
| 4,311,153 | 1/1982 | Smits | 128/785 |
| 4,332,259 | 6/1982 | McCorkle, Jr. | 128/786 |
| 4,402,329 | 9/1983 | Williams | 128/785 |
| 4,444,206 | * 4/1984 | Gold | |
| 4,497,326 | * 2/1985 | Curry | 607/123 |
| 4,567,901 | 2/1986 | Harris | 128/786 |
| 4,602,645 | 7/1986 | Barrington et al. | 128/786 |
| 4,649,938 | * 3/1987 | McArthur | 607/127 |

(List continued on next page.)

FOREIGN PATENT DOCUMENTS

| 452278A2 | 4/1990 | (EP) | A61N/1/05 |
|---|---|---|---|
| 0282047 | 9/1998 | (EP) | 607/127 |
| 94/22525 | 4/1993 | (WO) | A61N/1/05 |
| 96/15665 | 11/1994 | (WO) | A61N/1/05 |
| 97/40883 | 4/1996 | (WO) | A61N/1/05 |

Primary Examiner—Kennedy Schaetzle
(74) Attorney, Agent, or Firm—Schwegman, Lundberg, Woessner & Kluth, P.A.

(57) ABSTRACT

An endocardial lead comprising an elongate body having a first defibrillation coil electrode, a second defibrillation coil electrode and a first pacing/sensing electrode. The first defibrillation coil electrode has a first end and a second end, where the first end is at or near the distal end of the elongate body and the second end spaced longitudinally from the distal end. The first pacing/sensing electrode is spaced longitudinally along the peripheral surface from the second end of the first defibrillation coil electrode. The second defibrillation coil electrode is spaced longitudinally along the peripheral surface from the first pacing/sensing electrode to afford positioning the first defibrillation coil longitudinally adjacent an apical location of the right ventricle of a heart with the first pacing/sensing electrode within the right ventricle of the heart and the second defibrillation coil within the right atrial chamber or a major vein leading to the right atrial chamber of the heart. The elongate body further includes a curved portion on which the first pacing/sensing electrode is positioned such that the first pacing/sensing electrode extends beyond the peripheral surface of the elongate body to engage the tissue of the heart. The first pacing/sensing electrode further includes a retaining element, where the retaining element is adapted to be embedded in the right ventricle of the heart to secure the first pacing/sensing electrode and the elongate body of the endocardial lead to the right ventricle of the heart.

59 Claims, 11 Drawing Sheets

U.S. PATENT DOCUMENTS

| | | | | |
|---|---|---|---|---|
| 4,662,382 | | 5/1987 | Sluetz et al. | 128/785 |
| 4,667,686 | | 5/1987 | Peers-Travarton | 128/785 |
| 4,721,115 | | 1/1988 | Owens | 128/713 |
| 4,922,927 | | 5/1990 | Fine et al. | 128/786 |
| 4,953,564 | | 9/1990 | Berthelsen | 128/784 |
| 4,962,767 | * | 10/1990 | Brownlee | 607/123 |
| 4,967,766 | | 11/1990 | Bradshaw | 128/785 |
| 4,972,848 | | 11/1990 | DiDomenico et al. | 128/785 |
| 5,002,067 | | 3/1991 | Berthelsen et al. | 128/786 |
| 5,044,375 | | 9/1991 | Bach, Jr. et al. | 128/786 |
| 5,050,001 | | 9/1991 | Kupersmith et al. | 128/419 D |
| 5,107,834 | | 4/1992 | Ideker et al. | 128/419 |
| 5,111,811 | * | 5/1992 | Smits | 607/127 |
| 5,144,960 | * | 9/1992 | Mehra et al. | 607/127 |
| 5,152,299 | | 10/1992 | Soukup | 128/785 |
| 5,217,028 | * | 6/1993 | Dutcher et al. | 607/127 |
| 5,269,319 | | 12/1993 | Schulte et al. | 128/786 |
| 5,324,327 | | 6/1994 | Cohen | 607/122 |
| 5,387,233 | * | 2/1995 | Alferness et al. | 607/126 |
| 5,411,527 | | 5/1995 | Alt | 607/5 |
| 5,476,499 | * | 12/1995 | Hirschberg | 607/123 |
| 5,476,502 | | 12/1995 | Rubin | 607/127 |
| 5,522,874 | * | 6/1996 | Gates | 607/127 |
| 5,534,022 | * | 7/1996 | Hoffmann et al. | 607/122 |
| 5,545,201 | | 8/1996 | Helland, et al. | 607/127 |
| 5,545,205 | | 8/1996 | Schulte et al. | 607/123 |
| 5,571,163 | | 11/1996 | Helland | 607/123 |
| 5,628,778 | | 5/1997 | Kruse et al. | 607/123 |
| 5,628,779 | * | 5/1997 | Bornzin et al. | 607/123 |
| 5,662,698 | * | 9/1997 | Altman et al. | 607/123 |
| 5,674,272 | | 10/1997 | Bush et al. | 607/122 |
| 5,683,447 | * | 11/1997 | Bush et al. | 607/126 |
| 5,755,761 | * | 5/1998 | Obino | 607/123 |
| 5,772,693 | | 6/1998 | Brownlee | 607/123 |
| 5,837,006 | * | 11/1998 | Ocel et al. | 607/127 |
| 5,851,227 | | 12/1998 | Spehr | 607/126 |
| 5,876,431 | | 3/1999 | Spehr et al. | 607/126 |
| 5,964,795 | | 10/1999 | McVenes et al. | 607/122 |
| 5,978,705 | * | 11/1999 | KenKnight et al. | 607/5 |
| 6,055,457 | * | 4/2000 | Bonner | 607/126 |

* cited by examiner

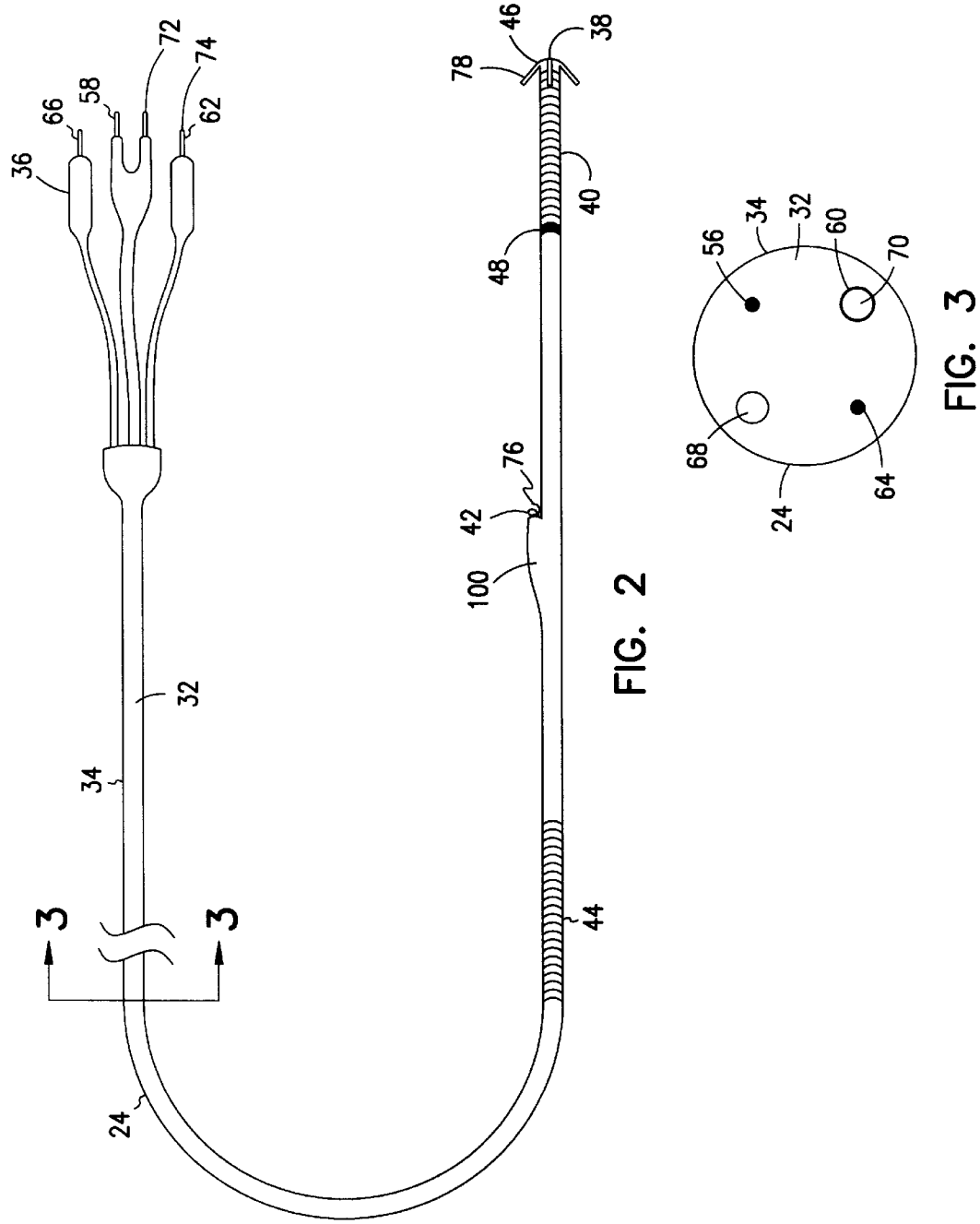

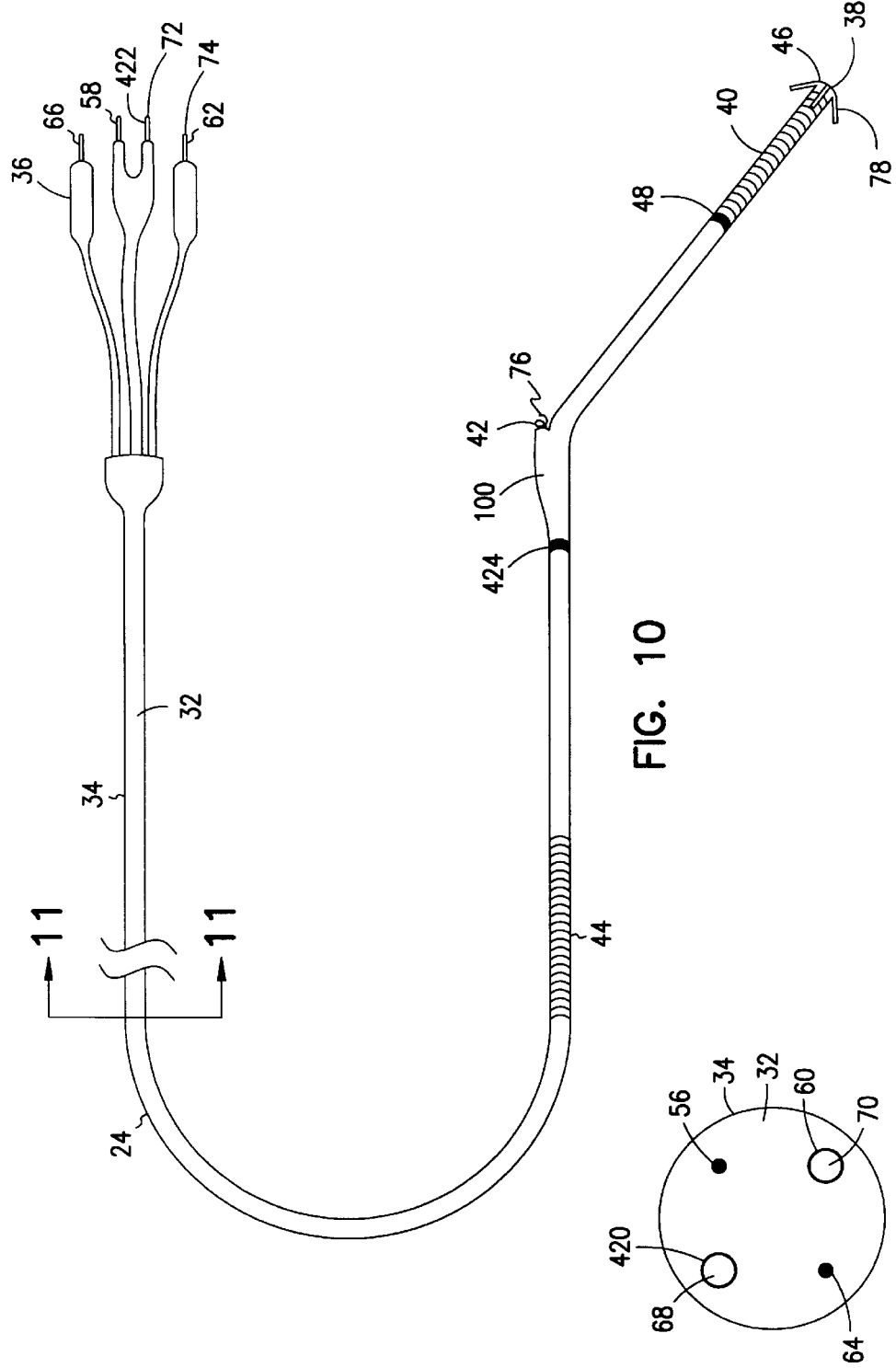

ENDOCARDIAL LEAD HAVING DEFIBRILLATION AND SENSING ELECTRODES WITH SEPTAL ANCHORING

TECHNICAL FIELD

The present invention relates generally to medical devices and in particular to implantable endocardial catheters for use with medical devices.

BACKGROUND OF THE INVENTION

Ventricular fibrillation of the heart is characterized by fine, rapid, fibrillatory movements of the ventricular muscle that replace the normal cardiac contraction. Since very little pumping action occurs during ventricular fibrillation, the situation is fatal unless quickly corrected by cardiac conversion. During conversion, defibrillation level electrical energy is applied to the heart in an attempt to depolarize the myocardial tissue of the heart and allow a normal sinus rhythm to be reestablished.

One theory that has been proposed to explain the mechanism of conversion by the application of defibrillation electrical current is the critical mass hypothesis. The critical mass hypothesis suggests that it is not necessary to halt all fibrillation activity in order to have defibrillation occur, but that it is sufficient to halt only a "critical mass" (perhaps 75%) of the myocardium in the ventricles. In this theory, the assumption is made that if all fibrillation activity is localized to a region smaller than the critical mass of myocardium, the remaining fibrillation activity is not capable of maintaining fibrillation and will die out after one or two cycles, resulting in normal sinus rhythm.

Implantable cardioverter/defibrillators (ICDs) have been successfully used to treat patients who have experienced one or more documented episodes of hemodynamically significant ventricular tachycardia or ventricular fibrillation. The basic ICD consists of a primary battery, electronic circuitry to control both the sensing of the patient's cardiac signals and the delivery of electrical shocks to the patient's heart, and a high-voltage capacitor bank housed within a hermetically sealed titanium case. One or more catheter leads having defibrillation electrodes are implanted within the heart of the patient or on the epicardial surface of the patient's heart. The catheter leads are then coupled to the implantable housing and the electronic circuitry of the ICD and are used to deliver defibrillation level electrical energy to the heart.

It has been suggested that a minimum and even (i.e., similar in all parts of the ventricles) potential gradient generated by a defibrillation level shock is necessary for effective cardiac defibrillation. This potential gradient is affected, and thus determined, by the voltage of the shock and the electrode configuration employed. It has also been suggested that a maximum potential gradient also exists that, beyond this value, deleterious electrophysiological and mechanical effects may occur, such as new arrhythmias, myocardial necrosis, or contractile dysfunction. Therefore, how and where defibrillation electrodes are placed on and/or within the heart has a major effect on whether or not a critical mass of cardiac tissue is captured during a defibrillation attempt.

Endocardial defibrillation catheters, those not requiring a thoracotomy to be place on the heart, have a major advantage over the epicardial lead systems by reducing the morbidity, mortality, and cost of thoracotomy procedures. However, a major problem with these systems is the potential for high defibrillation thresholds as compared to system employing epicardial defibrillation electrodes. Changes to the waveform of the defibrillation shock and to the combinations of endocardial leads implanted into a patient and the current pathways used can result in efficacious defibrillation therapy being delivered to the patient.

The easiest and most convenient way to perform the implantation of a fully transvenous system is to use only one endocardial lead with both sensing and pacing and defibrillation capabilities. One such endocardial lead is sold under the trademark ENDOTAK C (Cardiac Pacemaker, Inc./ Guidant Corporation, St. Paul, Minn.), which is a tripolar, tined, endocardial lead featuring a porous tip electrode (placed in the apex of the right ventricular) that serves as the cathode for intracardiac right ventricular electrogram rate sensing and pacing, and two defibrillation coil electrodes, with the distal one serving as the anode for rate sensing and as the cathode for morphology sensing and defibrillation which the proximal coil electrode positioned within the superior vena cava functions as the anode for defibrillation.

However, single body endocardial leads used for both defibrillation and rate sensing have been reported to suffer technical inadequacies that may pose significant risks to the patient. Endocardial electrograms obtained from integrated sense/pace-defibrillation leads have been shown to be affected after shock delivery, with their amplitude decreasing to such a significant degree that arrhythmia redetection is dangerously compromised. As already mentioned above, obtaining adequate defibrillation thresholds has been a major problem with the nonthoracotomy endocardial lead systems. Therefore, a need exists to design an endocardial lead system that effectively reduces defibrillation thresholds and allow for reliable post-defibrillation shock sensing and pacing.

SUMMARY OF THE INVENTION

The present invention provides a single body endocardial lead, and an implantable apparatus for its use, that reduces defibrillation thresholds and improves post-defibrillation shock therapy redetection. One aspect of these improvements is the placement of the electrodes on the endocardial lead. The electrode configuration on the endocardial lead improves the potential gradient generated by a defibrillation level shock, which increases the effectiveness of the cardiac defibrillation shock and reduces the defibrillation threshold as compared to conventional endocardial leads. Also, the position of the pacing electrode relative to the defibrillation electrodes provides for a more reliable and accurate post-defibrillation shock electrogram. Furthermore, the reduction in defibrillation thresholds allows for reduced battery consumption of the implantable device, potentially prolonging the life of the device and/or allowing for an overall reduction in the size of the device.

The endocardial lead of the present invention has an elongate body with a peripheral surface, a proximal end, a distal end, and a first defibrillation coil electrode and a first pacing/sensing electrode on the peripheral surface. The first defibrillation coil electrode is positioned on the endocardial lead at or near the distal end of the elongate body. The first pacing/sensing electrode is spaced longitudinally along the peripheral surface from the first defibrillation coil electrode to afford positioning both the first defibrillation coil and the first pacing/sensing electrode in a right ventricle of a heart. In one embodiment, the endocardial lead is positioned within the right ventricle of the heart with the first defibrillation coil electrode positioned longitudinally adjacent the right ventricular septal wall. In an additional embodiment, the endocardial lead is positioned within the right ventricle of the heart with the first defibrillation coil electrode positioned directly within the ventricular apex, where the first defibrillation coil is longitudinally adjacent to the apex of the right ventricle of the heart.

In an additional embodiment of the invention, the endocardial lead further includes a second defibrillation coil electrode on the peripheral surface. The second defibrillation coil electrode is spaced longitudinally along the peripheral surface from the first pacing/sensing electrode to afford positioning the first defibrillation coil and the first pacing/sensing electrode within the right ventricle and the second defibrillation coil within the supraventricular region of the heart. In one embodiment, the second defibrillation coil electrode is positioned within a right atrial chamber or a major vein leading to the right atrial chamber of the heart.

Different types and configurations of first pacing/sensing electrodes can be used with the endocardial lead of the present invention. In one embodiment, the first pacing/sensing electrode includes a retaining element integrated into or positioned adjacent the first pacing/sensing electrode. The retaining element is adapted to be embedded in the tissue of the right ventricle of the heart to secure the first pacing/sensing electrode, and the elongate body of the endocardial lead, to the right ventricle of the heart. In one embodiment, the retaining element is a helical wire which used to secure the first pacing/sensing electrode to the cardiac tissue of the ventricular septum.

In an additional embodiment, the peripheral surface of the elongate body defines an electrode housing having an opening, the housing being adapted to sheathe the first pacing/sensing electrode and the retaining element and through which the first pacing/sensing electrode and/or the retaining element extends from the peripheral surface to engage the right ventricular chamber of the heart. A stylet lumen extends through the elongate body of the endocardial lead to the first pacing/sensing electrode and is adapted to receive a stylet that is used for extending and rotating the first pacing/sensing electrode and the retaining element to embed the retention element of the first pacing/sensing electrode into the right ventricle of the heart.

In an alternative embodiment, the elongate body of the endocardial lead further has a curved portion spaced between the proximal end and the distal end. The curved portion has an outer radial surface and an inner radial surface, where the outer radial surface generally has a larger radius of curvature then the inner radial surface. The electrode housing of the first pacing/sensing electrode is positioned generally on the outer radial surface of the curved portion such that when the first pacing/sensing electrode is extended beyond the peripheral surface of the elongate body to engage the tissues of the heart it is along an axis that is essentially parallel with a longitudinal axis of the proximal end of the elongate body. In one embodiment, the curved portion creates an angle of between approximately 45 to 60 degrees relative to a longitudinal axis of the distal end and a longitudinal axis of the proximal end of the elongate body.

In an alternative embodiment, the curved elongate body has a first pacing/sensing electrode that is a porous woven mesh having a semi-spherical shape located on the peripheral surface of the elongate body. The porous woven mesh semi-spherically shaped first pacing/sensing electrode is generally positioned on the outer radial surface of the curved portion such that when the endocardial lead is implanted in the body, the first defibrillation coil electrode is positioned in the right ventricular apex and the first pacing/sensing electrode is in physical contact with the tissues of the right ventricle chamber of the heart. In one embodiment, the first pacing/sensing electrode is positioned on the septal wall of the right ventricle of the heart.

In an alternative embodiment, the first pacing/sensing electrode is an annular or semi-annular ring electrode, as are known in the art, generally positioned on the outer radial surface of the curved portion such that when the endocardial lead is implanted in the body, the first defibrillation coil electrode is positioned in the right ventricular apex and the first pacing/sensing electrode is in physical contact with the tissues of the right ventricle chamber of the heart.

BRIEF DESCRIPTION OF DRAWINGS

In the drawings, where like numerals describe like components throughout the several views:

FIG. 2 is a schematic view of one embodiment of an endocardial lead according to the present invention;

FIG. 3 is a cross-sectional view of the embodiment of an endocardial lead according to FIG. 2 taken along the lines 3—3;

FIG. 10 is a schematic view of an embodiment of an endocardial lead according to the present invention;

FIG. 11 is a cross-sectional view of the embodiment of an endocardial lead according to FIG. 10 taken along the lines 11—11.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Figure 1:
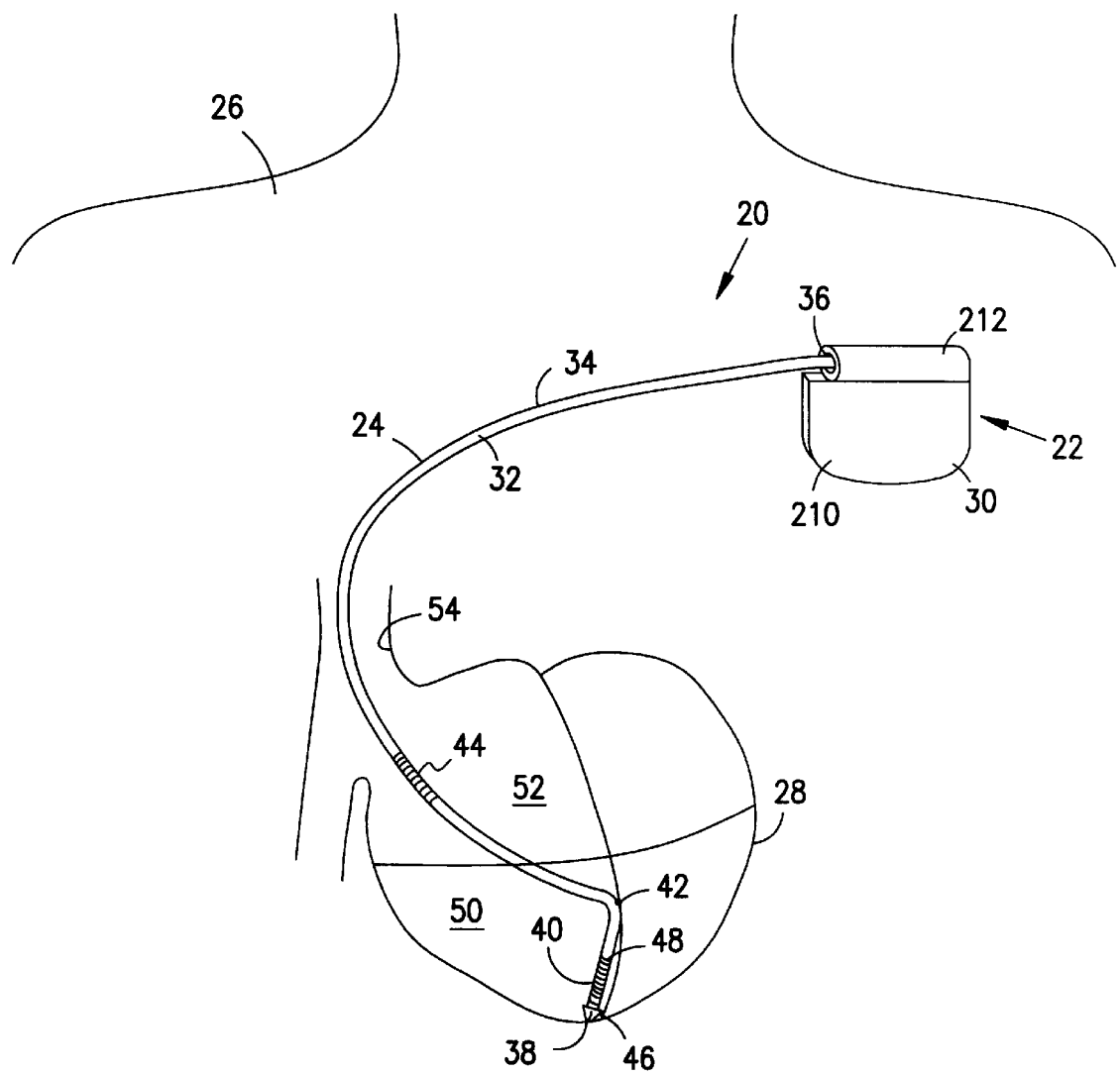
FIG. 1 is a schematic view of an implantable cardioverter/defibrillator with one embodiment of an endocardial lead implanted in a heart from which segments have been removed to show details.

Referring now to FIG. 1 of the drawings, there is shown one embodiment of an apparatus 20 including a cardioverter/defibrillator 22 physically and electrically coupled to an endocardial lead 24. The apparatus 20 is implanted in a human body 26 with portions of the endocardial lead 24 inserted into a heart 28 to detect and analyze electric cardiac signals produced by the heart 28 and to provide electrical energy to the heart 28 under certain predetermined conditions to treat ventricular arrhythmias, including ventricular tachyarrhythmias and ventricular fibrillation, of the heart 28.

The endocardial lead 24 comprises an elongate body 32 having a peripheral surface 34, a proximal end 36 and a distal end 38. The endocardial lead 24 also includes one or more defibrillation coil electrodes and one or more pacing/sensing electrodes. In one embodiment, the endocardial lead 24 has a first defibrillation coil electrode 40, a first pacing/ sensing electrode 42 and a second defibrillation coil electrode 44 attached to the peripheral surface 34 of the elongate body 32.

In one embodiment the first defibrillation coil electrode 40 and the second defibrillation coil electrode 44 are helically wound spring electrodes as are known in the art. The first defibrillation coil electrode 40 and the second defibrillation coil electrode 44 have surface areas that are between 200 to 1000 square millimeters, where a surface area of 500 square millimeters for the first defibrillation coil electrode 40 and a surface area of 800 square millimeters for the second defibrillation coil electrode 44 are acceptable values. In an additional embodiment, the first defibrillation coil electrode 40 and the second defibrillation coil electrode 44 have a helical coil diameter of between 2.5 to 4.0 millimeters and a length in the range of 2 to 6 cm, 3 to 6 cm, 4 to 6 cm, 2 to 4 cm where 3 to 4 cm is an acceptable range.

The first defibrillation coil electrode 40 further includes a first end 46 and a second end 48, where the first end 46 is at or near the distal end 38 of the elongate body 32 and the second end 48 is spaced longitudinally along the peripheral surface from the first end 46 of the first defibrillation coil electrode 40 and the distal end 38 of the elongate body 32. In one embodiment the first end 46 of the first coil electrode 40 forms a portion of the distal end 38 of the elongate body 32. In an alternative embodiment, the first end 46 of the first coil electrode 40 is spaced longitudinally along the peripheral surface 34 from the distal end 38 by a distance in the range of 0 to 7 millimeters.

The first pacing/sensing electrode 42 is spaced longitudinally along the peripheral surface 34 from the second end 48 of the first defibrillation coil electrode 40 by a distance in the range of 1 to 10 centimeters, where an acceptable range is between 1 to 3 centimeters. In one embodiment, the spacing of the first defibrillation coil electrode 40 and the first pacing/sensing electrode 42 is to afford positioning the first defibrillation coil 40 and the first pacing/sensing electrode 42 in the right ventricle 50 of the heart 28. In one embodiment, the first defibrillation coil electrode 40 is implanted into the apical location of the right ventricle 50 such that the first defibrillation coil electrode 40 is positioned longitudinally adjacent the septal location of the right ventricle 50 of the heart 28 and the first pacing/sensing electrode 42 is in physical contact with the septal wall of the right ventricle 50.

The second defibrillation coil electrode 44 is spaced longitudinally along the peripheral surface 34 from the first pacing/sensing electrode 42 by a distance in the range of 8 to 15 centimeters. In one embodiment, the spacing of the second defibrillation coil electrode 44 and the first defibrillation coil electrode 40 is to afford positioning the second defibrillation coil electrode 44 within a right atrial chamber 52 or a major vein 54 leading to the right atrial chamber 52 when the first defibrillation coil electrode 40 and the first pacing/sensing electrode 42 are positioned within the right ventricular chamber 50. In one embodiment, the major vein 54 leading to the heart right atrial chamber 52 is the superior vena cava.

Referring now to FIGS. 2 and 3 there is shown one embodiment of the endocardial lead 24 according to the present invention. A first electrical conductor 56 is shown extending longitudinally within the elongate body 32 from a first contact end 58 at the proximal end 36 and is electrically connected to the first defibrillation coil electrode 40. A second electrical conductor 60 is also shown extending longitudinally within the elongate body 32 from a second contact end 62 at the proximal end 36 and is electrically connected to the first pacing/sensing electrode 42. Finally, a third electrical conductor 64 is shown extending longitudinally within the elongate body 32 from a third contact end 66 at the proximal end 36 and is electrically connected to the second defibrillation coil electrode 44. In one embodiment, the first contact end 58, the second contact end 62 and the third contact end 66 are tubular or solid metallic pins which are constructed of titanium, stainless steel, or MP35N.

The endocardial lead has at least one stylet lumen extending longitudinally in the elongate body 32. In one embodiment, the elongate body 32 has a first stylet lumen 68 and a second stylet lumen 70, where the first stylet lumen 68 extends from a first inlet end 72 at the proximal end 36 to the distal end 38. The first stylet lumen 68 is adapted to receive a guide stylet for stiffening and shaping the endocardial lead 24 during the insertion of the endocardial lead 24 into the heart 28. The second stylet lumen 70 extends from a second inlet end 74 at the proximal end 36 to the first pacing/sensing electrode 42. In one embodiment, the second stylet lumen 70 is formed by the second electrical conductor 60, which has an elongate helical coil configuration as is known in the art.

In an additional embodiment, the first pacing/sensing electrode 42 includes a retaining element 76, where the retaining element 76 is adapted to be embedded in the right ventricle 50 of the heart 28. The retaining element 76 is designed to secure the first pacing/sensing electrode 42 and the elongate body 32 of the endocardial lead 24 to the heart 28. In one embodiment, the retaining element 76 is intended to secure the first pacing/sensing electrode 42 and the elongate body 32 of the endocardial lead 24 at an endocardial position within the right ventricle 50 of the heart 28.

In one embodiment, the retaining element 76 is a straight segment of wire. The straight segment of wire has a proximal and a distal end, where the distal end is sharpened to a point and further includes a retaining barb 77. The retaining barb at the distal end projects away from the peripheral surface of the straight wire and toward the proximal end of the straight wire and is intended to engage and embed into the tissue of the heart. In an additional embodiment, the retaining element 76 is a wire shaped into a helical corkscrew like projection, where the wire has a proximal end and a distal end. In one embodiment, the distal end is sharpened to a point which is adapted to engage and embed into the ventricular tissue of the heart. In an additional embodiment, the proximal end of the retaining element 76 is secured within the first pacing/sensing electrode 42 by welding the proximal end to the first pacing/sensing electrode. In an alternative embodiment, the proximal end of the retaining element 76 is physically secured to the first pacing/sensing electrode 42 by engaging the proximal end and the first pacing/sensing electrode 42 so as to create a friction fit between the two elements.

In a further embodiment, the retaining element 76 forms a portion of the first pacing/sensing electrode, where the wire retaining element emanates from and extends away from an outer surface of the first pacing/sensing electrode 42. In an additional embodiment, the helical wire of the retaining element 76 extends around the peripheral surface of the first pacing/sensing electrode, extending away from the outer surface of the first pacing/sensing electrode. In an alternative embodiment, the retaining element 76 is a hooked projection having a sharped distal end which is used to engage the tissues of the right ventricle of the heart and to secure the first pacing/sensing electrode 42 and the elongate body 32 to the heart 28.

Figure 4:
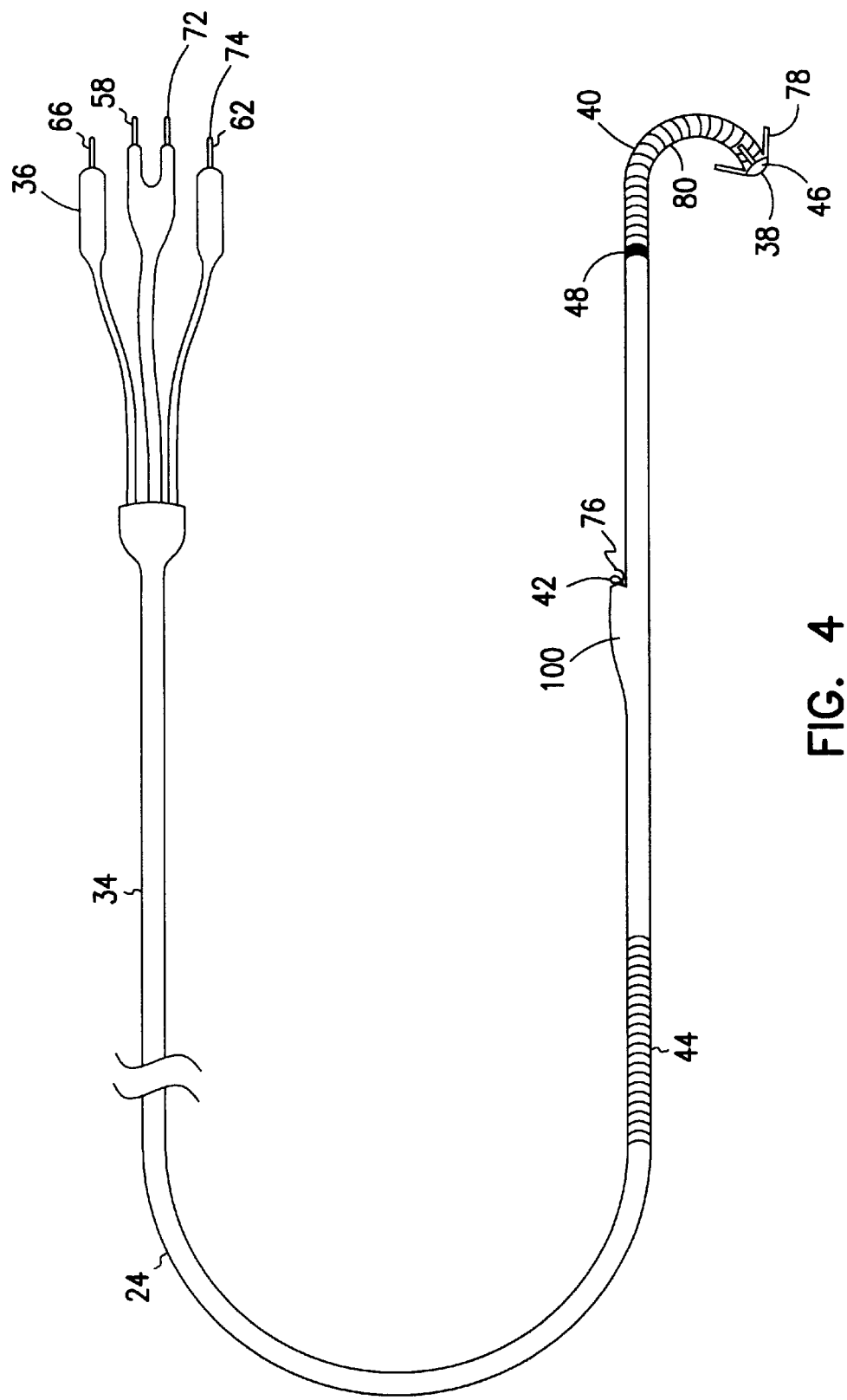
FIG. 4 is a schematic view of one embodiment of an endocardial lead according to the present invention.
Figure 5:
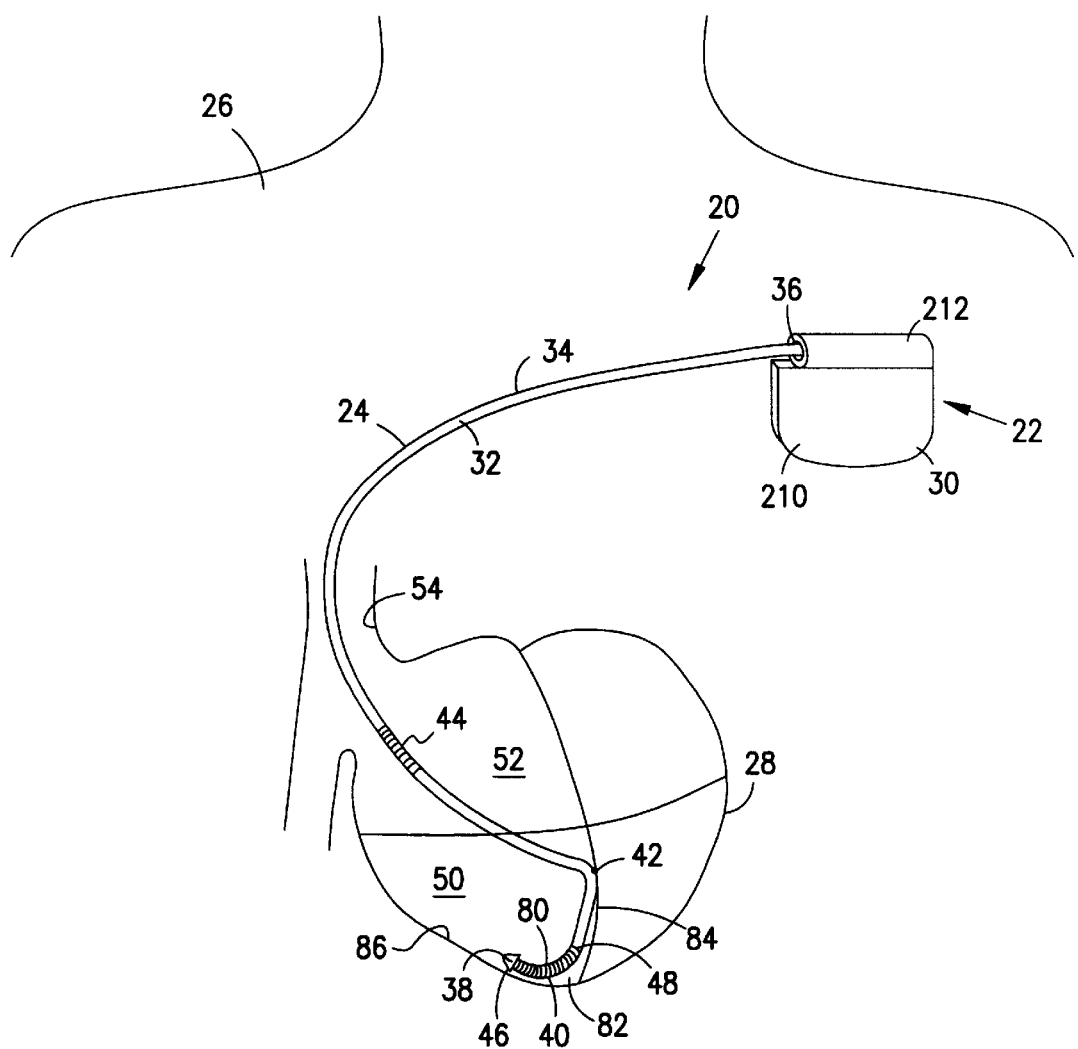
FIG. 5 is a schematic view of an implantable cardioverter/defibrillator with one embodiment of an endocardial lead implanted in a heart from which segments have been removed to show details.

Referring now to FIGS. 4 and 5, there is shown an additional embodiment of an endocardial lead 24, in which the elongate body 32 of the endocardial lead 24 further includes an arc-shaped end portion 80. In one embodiment, the arc-shaped end portion 80 curves away from the long-axis of the elongate body 32 to create a "J-tip" at the distal end 38 of the endocardial lead 24. In an alternative embodiment, the arc-shaped end portion 80 curves away from the long-axis of the elongate body 32 to create a "L-tip" at the distal end 38 of the endocardial lead 24, where the distal end 38 of the elongate body 32 is positioned perpendicularly to the long-axis of the elongate body 32. The arc-shaped end portion 80 is adapted to be positioned within and adjacent to the apex 82 of the right ventricle 50.

In one embodiment, the arc-shaped end portion 80 curves away from the longitudinal axis of the proximal end 36 of the elongate body 32 in a direction that is opposite the side on which the first pacing/sensing electrode 42 is positioned. In one embodiment, this configuration of the endocardial lead 24 allows the first pacing/sensing electrode 42 to be implanted or positioned along the septal wall 84 of the right ventricle 50. As the elongate body 32 extends down and adjacent the septal wall 84 the arc-shaped end portion 80 begins to curve or deflect away from the septal wall 84 as the elongate body 32 extends into the apex 82 of the right ventricle 50. The arc-shaped end portion 80 is adapted to be positioned in the apex 82 of the right ventricle 50. As a result, the first defibrillation coil electrode 40 is located in the apex 82 and along the endocardial wall 86 of the right ventricle 50. Depending upon the length of the first defibrillation coil electrode 40, a portion of the electrode extends along the endocardial wall 86 of the right ventricle 50 from the region of the apex 82 of the right ventricle 50.

In an alternative embodiment, the arc-shaped end portion 80 curves away from the longitudinal axis of the proximal end 36 of the elongate body 32 in a direction that is perpendicular to the side on which the first pacing/sensing electrode 42 is positioned. In an additional embodiment, the arc-shaped end portion 80 curves away from the longitudinal axis of the proximal end 36 of the elongate body 32 in any direction that is between being opposite or perpendicular to the side on which the first pacing/sensing electrode 42 is positioned on the peripheral surface 34 of the elongate body 32. Generally, this configuration of the endocardial lead 24 allows the first pacing/sensing electrode 42 to be implanted or positioned along the septal wall 84 of the right ventricle 50. As the elongate body 32 extends down and adjacent the septal wall 84 the arc-shaped end portion 80 begins to curve or deflect away from the longitudinal axis of the elongate body 32 along the septal wall as the elongate body 32 extends into the apex 82 of the right ventricle 50. The arc-shaped end portion 80 is adapted to be positioned in the apex 82 of the right ventricle 50 so that the first defibrillation coil electrode 40 is located along both the endocardial wall 86 and the septal wall 84 in the region of the apex 82 of the right ventricle 50. Depending upon the length of the first defibrillation coil electrode 40, a portion of the electrode extends along the endocardial wall 86 of the right ventricle 50 from the region of the apex 82 of the right ventricle 50.

In one embodiment of creating the arc-shaped end portion 80 of the endocardial lead 24, the first defibrillation coil electrode 40 is formed with a mechanical bias in the electrode structure. In one embodiment, the mechanical bias in the first defibrillation coil electrode 40 is imparted into the electrode during the winding of the electrode. In an alternative embodiment, the mechanical bias is created by mechanically deforming the electrode after it has been wound. In an alternative embodiment, the polymer structure of the elongate body 32 is modified to create the arc-shaped end portion 80. In one embodiment, the arc-shaped end portion 80 is constructed of a polymer having an enhanced stiffness relative to the remainder of the elongate body 32. In an alternative embodiment, the arc-shaped end portion 80 is molded into the elongate body 32 during the construction of the elongate body 32.

In one embodiment, the curvature of the arc-shaped end portion 80 generally conforms to the curvature of the apex 82 region. This radius of curvature maximizes direct contact between the first defibrillation coil electrode 40 and the endocardial tissue of the right ventricle 50. Because the shape of diseased hearts varies considerably, an optimized radius of curvature will be determined on a patient by patient basis.

In one embodiment, the arc-shaped end portion 80 has a semicircular shape. In an alternative embodiment, the arc-shaped end portion 80 has a parabolic shape. In an additional embodiment, the arc-shaped end portion 80 has a small radius of curvature which creates an abrupt angular deflection in the elongate body of the endocardial lead 24. In one embodiment, the radius of curvature creates an angle of between approximately 10 to 70 degrees relative to a longitudinal axis of the distal end 38 and a longitudinal axis of the proximal end 36 of the elongate body 32. In an alternative embodiment, the radius of curvature is in the range of 0.25 to 1 cm, 0.5 to 1 cm, 1 to 2 cm, 1 to 3 cm when a radius of curvature of approximately 1 cm is an acceptable value.

Figure 6A:
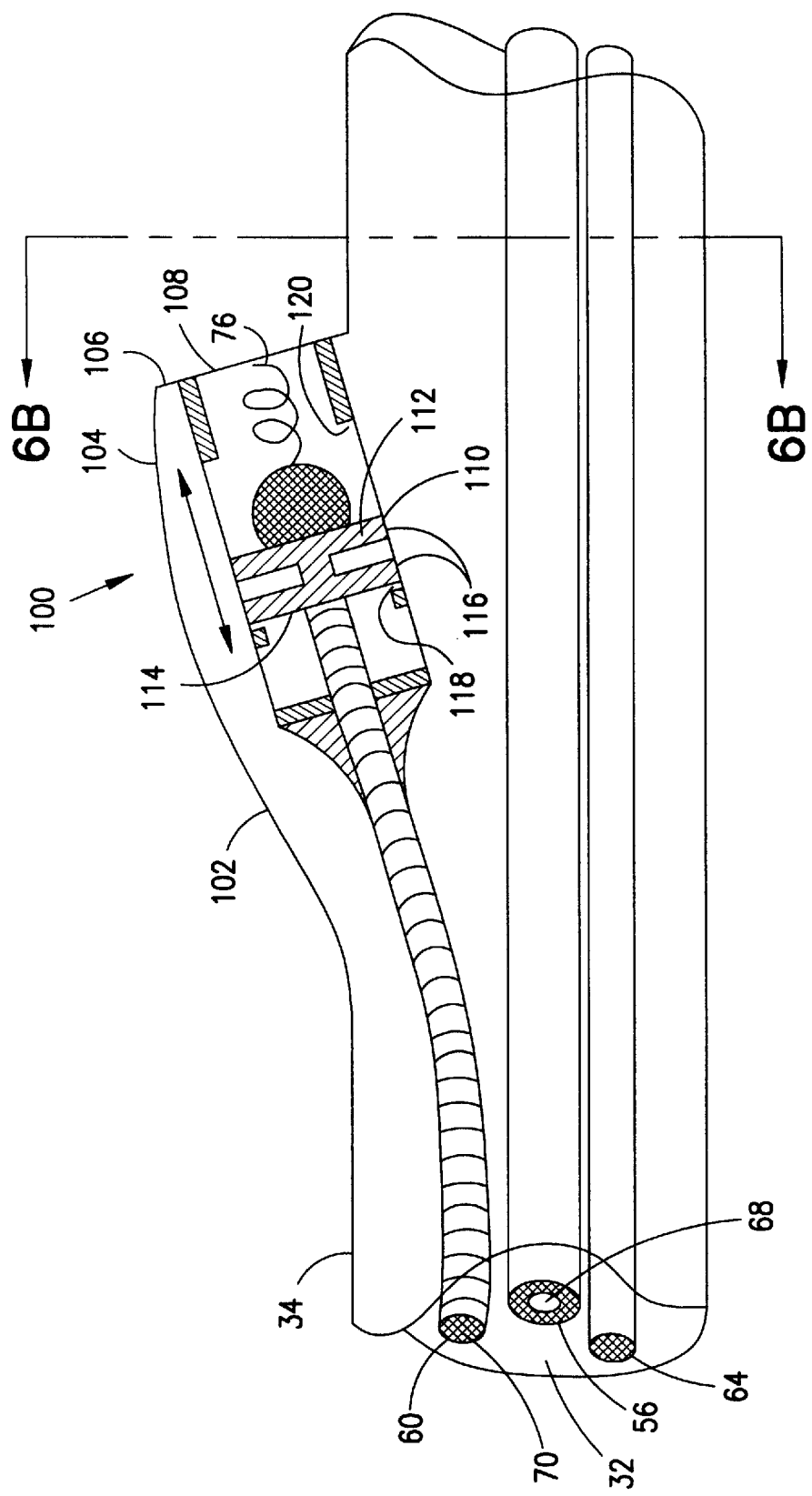
FIG. 6 (A–C) are enlarged segmentary views of one embodiment of an electrode housing on an endocardial lead according to the present invention.
Figure 6B:
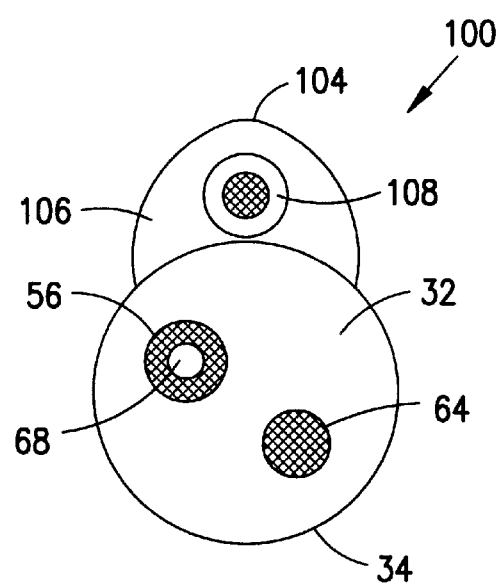
Figure 6C:
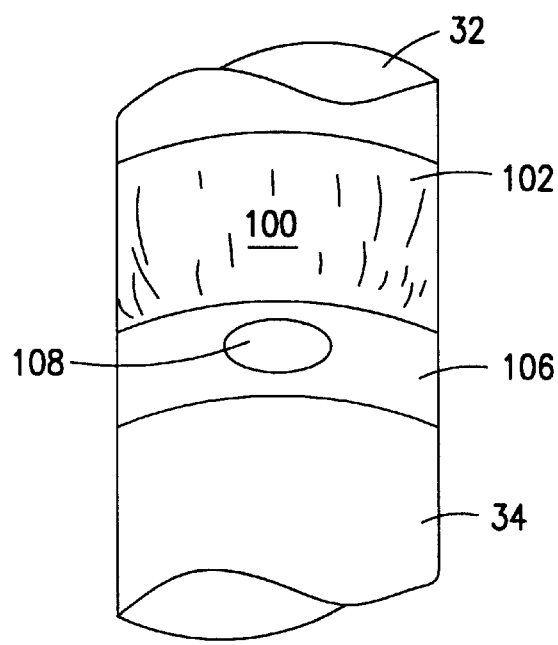

Referring now to FIG. 6 (A–C), there is shown an additional embodiment of the endocardial lead 24 in which the peripheral surface 34 of the elongate body 32 further defines an electrode housing 100 having walls defining an opening therethrough, and where the electrode housing 100 is adapted to sheathe the first pacing/sensing electrode 42 and through which the first pacing/sensing electrode 42 extends to engage the right ventricular chamber 50 of the heart 28.

In one embodiment, the electrode housing 100 is attached to and projects away from the peripheral surface 34 of the elongate body 32. The electrode housing 100 has a first wall portion 102 that partially encircles and projects away from the peripheral surface 34 in an arcuate fashion until it reaches an upper limit 104 at which point the first wall portion 102 becomes parallel with the longitudinal axis of the elongate body 32. In one embodiment, the cross-sectional shape of the electrode housing 100 at the upper limit 104 of the first wall portion 102 is that of a partial ellipse.

The electrode housing 100 also includes a second wall portion 106, where the second wall portion 106 is positioned essentially perpendicular to the first wall portion 102 so that the second wall portion 106 projects from the upper limit 104 of the first wall portion 102 to a portion of the peripheral surface 34 of the elongate body 32. The second wall portion 106 also defines the opening 108 through the electrode housing 100, where the opening 108 through the electrode housing 100 is coupled to an opening through the peripheral surface 34 of the elongate body 32. The second electrical conductor 60 extends through the opening in the elongate body 32 and into the opening 108 defined by the second wall portion 106 of the electrode housing 100. In one embodiment, the second wall portion 106 defines a tubular shaped opening 108 through the electrode housing 100.

In one embodiment, the second electrical conductor 60 is coupled to and makes an electrical connection with a moveable element 110 which is housed within the opening 108 of the electrode housing 100. The moveable element 110 has an outer surface 112, an inner surface 114 and a circumferential surface 116, where the circumferential surface 116 is sealed against the second wall portion 106 of the opening 108.

In one embodiment, the moveable element 110 is intended to move longitudinally within the opening 108 from a first or recessed position 118 to a second or extended position 120 and also to rotate on the circumferential surface 116 due to force applied to the inner surface of the sleeve by a guide stylet inserted through the second stylet lumen 70, where the second stylet lumen 70 is adapted to receive a stylet for extending and rotating the first pacing/sensing electrode 42 to embed the retaining element 76 of the first pacing/sensing electrode 24 into the right ventricle 50 of the heart 28.

The second electrical conductor 60 is secured to the elongate body 32 at the location where it emerges from the opening through the peripheral surface 34 of the elongate body 32 into the opening 108 through the electrode housing 100. The helical coil construction of the second electrical conductor 60 then allows the conductor to extend in a spring like fashion as the moveable element 110 moves between the first position 118 and the second position 120.

In one embodiment, the first pacing/sensing electrode 42 is coupled to the outer surface 112 of the moveable element 110. In the first position 118 of the moveable element 110, the first pacing/sensing electrode 42 and the retaining element 76 are housed within the opening 108 in the electrode housing 100. After the moveable element 110 is advanced to the second position 120, both the retaining element 76 and the first pacing/sensing electrode 42 extend a predetermined distance beyond the second wall portion 106 of the electrode housing 100. In one embodiment, up to 3 centimeters is an acceptable predetermined distance. In one embodiment, the retaining element 76 and the first pacing/sensing electrode 42 extend beyond the second wall portion 106 in plane that is essentially parallel to the longitudinal axis of the elongate body 32. In an alternative embodiment, the retaining element 76 and the first pacing/sensing electrode 42 extends beyond the second wall portion 106 in plane having an acute angle (less than 90 degrees) relative to the longitudinal axis of the elongate body 32.

In an additional embodiment, the elongate body further has a plurality of tines 78 at or adjacent the distal end 38, the plurality of tines 78 being circumferentially spaced and projecting both radially away from the peripheral surface 34 and toward the proximal end 36 of the elongate body 32. In one embodiment, the plurality of tines is constructed of the same material used to make the elongate body 32 of the endocardial lead 24.

In one embodiment, the elongate body 32 of the endocardial lead 24 is made by extrusion of an implantable polyurethane, silicone rubber or other implantable flexible biocompatible polymer. The length of the elongate body 32 of the endocardial lead 24 between the proximal end 36 and the distal end 38 is in the range of between 60 to 120 centimeters. In an additional embodiment, the elongate body 32 has a diameter of less than or equal to 4 millimeters. The electrical conductors 56, 60 and 64 are made of a MP35N nickel-cobalt alloy, or other electrical conductor metal as are known in the art. The first defibrillation coil electrode 40, the second defibrillation coil electrode 44, the first pacing/sensing electrode 42, the moveable element 110, and the retaining element 76 are made of an implantable metal such as platinum/iridium alloys, titanium or other implantable metals as are known in the art.

Experimental data indicate that the use of the endocardial lead 24 has the potential of reducing a patient's defibrillation strength requirements. Experimental tests on defibrillation energy requirements using both the endocardial lead 24 of the present invention and an endocardial lead sold under the trademark ENDOTAK (Cardiac Pacemaker, Inc./ Guidant Corporation, St. Paul, Minn.), in porcine and canine models indicate that the use of the endocardial lead 24 reduced defibrillation delivered energy requirements by 26% as compared to the use of the ENDOTAK lead. Also, the use of the endocardial lead 24 and the ENDOTAK lead in the same animal models showed that the use of the endocardial lead 24 reduced the average peak current requirements of 22% as compared to the use of the ENDOTAK lead.

The experimental endocardial defibrillation systems incorporated either the single-pass ENDOTAK or the endocardial lead 24 of the present invention with an implantable cardioverter/defibrillator sold under the trademark MINI II (Cardiac Pacemaker, Inc./ Guidant Corporation, St. Paul, Minn.), shell electrode to create a defibrillation electrode system sold under the trademark TRIAD, (Cardiac Pacemaker, Inc./ Guidant Corporation, St. Paul, Minn.). Both leads consisted of an approximately 3.4 cm long, 0.110 inch diameter distal and a 6.8 cm long, 0.110 inch diameter proximal tri-filar DBS spring shocking electrodes. The ENDOTAK lead had a standard porous tip pace/sense electrode with a tip-to-shocking electrode length of approximately 1.2 cm. Conversely, the endocardial lead 24 had the shocking electrode positioned at the end of the elongate body 32 with the first pacing/sensing electrode 42 approximately 1.2 cm proximal to the shocking electrode. In one embodiment, the first pacing/sensing electrode 42 consisted of a miniaturized electrode position within the helical coil wound around the outside diameter of the electrode. For purposes of the experimental procedure, the elongate body 32 further includes a curved portion, where the curved portion is positioned between the proximal end 36 and the distal end 38 of the elongate body 32. The curved portion has an outer radial surface and an inner radial surface, where the outer radial surface generally has a larger radius of curvature then the inner radial surface. The first pacing/sensing electrode 42 was positioned on the outer radial surface of the curved portion so that the first pacing/sensing electrode 42 extended beyond the peripheral surface 34 of the elongate body 32 along an axis that is essentially parallel with a longitudinal axis of the proximal end 36 of the elongate body 32 to engage the tissue of the heart 28. The curved portion of the endocardial lead 24 created an approximately 60 degree arc relative to a longitudinal axis of the distal end 38 and a longitudinal axis of the proximal end 36 of the elongate body 32 to facilitate septal positioning and to serve as a platform for the first pacing/sensing electrode 42.

Pacing and sensing characteristics and defibrillation strength requirements for each lead system were determined in six swine. Under fluoroscopic guidance, both lead systems were positioned into the right ventricular apex through a left external jugular venotomy. Once apically placed, each lead was advanced until the right ventricular shocking electrode was positioned into the anterior groove of the right ventricular out-flow tract against the septum. The MINI II shell electrode was subcutaneously implanted in the left pectoral region. For defibrillation trials, the right ventricular shocking electrode served as the cathode.

Pacing thresholds (0.5 ms pulse widths), impedances and sensing characteristics (R-wave amplitudes) were determined prior to the defibrillation trials using a SEAMED external stimulator (Redmond, Wash.). Defibrillation strength requirements (delivered energy, peak voltage and peak current) and system impedances for each lead system were determined using 80% fixed-tilt biphasic shocks generated from a LABVIEW directed current amplifier (National Instrument, Austin, Tex.). The defibrillation requirements, pacing thresholds and sensing characteristics of the two lead systems were compared using paired t tests.

Defibrillation strength requirements for the endocardial lead 24 was lower than with the ENDOTAK system. Delivered energy, peak voltage and peak current requirements were 32%, 17% and 25%, (p<0.01) respectively, lower with the endocardial lead 24 when applied to the TRIAD system as compared to the ENDOTAK TRIAD system. Although not statistically significant with the paired t-test, pacing and sensing characteristics of the endocardial lead 24 were different from the ENDOTAK system. Sensed R-wave amplitudes were 14% (p>0.05) lower with the endocardial lead 24 system than with the ENDOTAK system. Pacing thresholds were 38% lower (0.3V, p>0.05) with the ENDOTAK passive electrode than with the retractable miniaturized positive fixation electrode of the endocardial lead 24 system. The endocardial lead 24 test lead system impedance was 12% higher than the ENDOTAK system.

Figure 7:
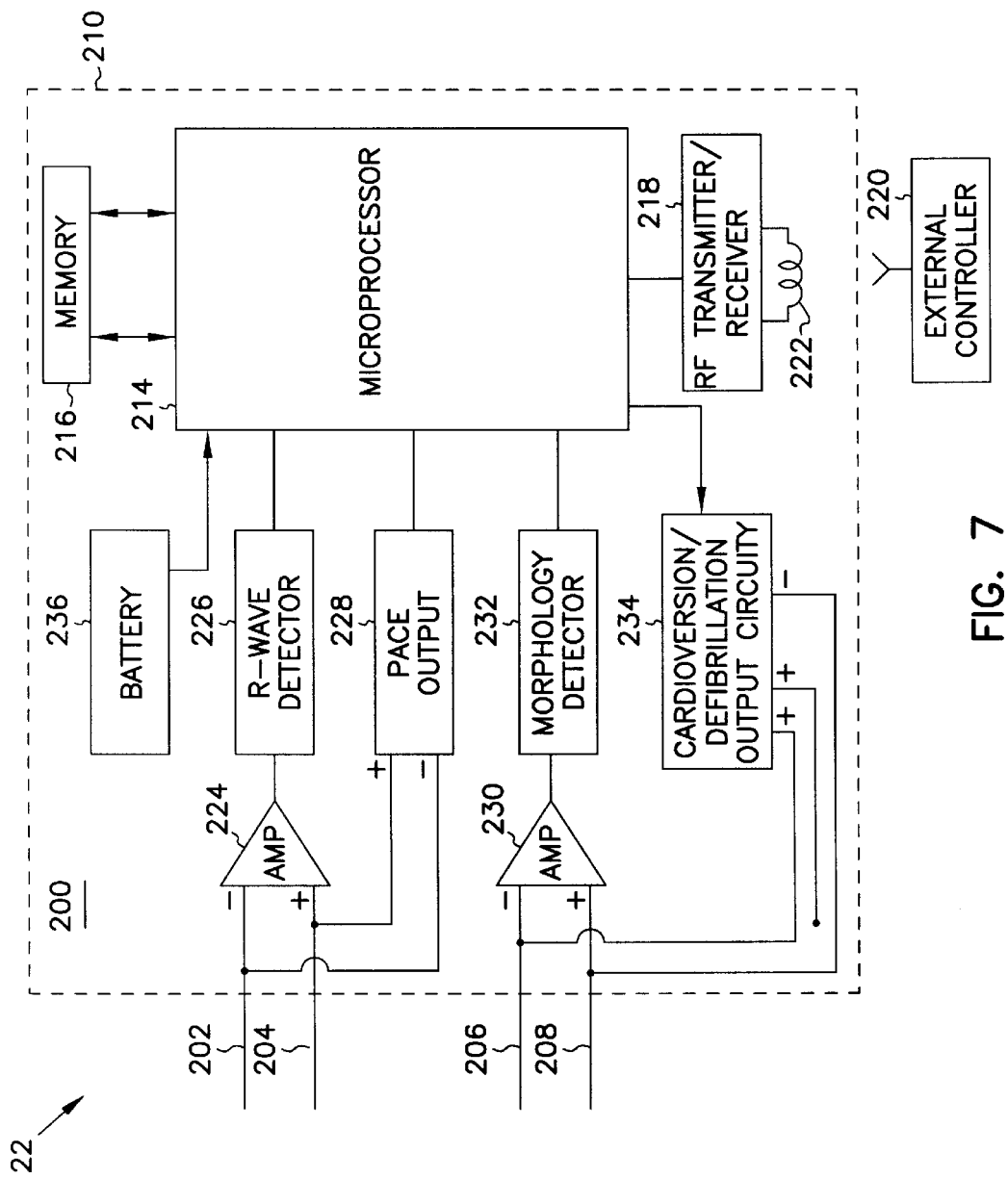
FIG. 7 is a block diagram of an implantable cardioverter/defibrillator according to the present invention.

Referring now to FIG. 7, there is shown one embodiment of an electronics block diagram of the cardioverter/defibrillator 22. The cardioverter/defibrillator 22 includes electronic control circuitry 200 for receiving cardiac signals from the heart 28 and delivering electrical energy to the heart 28. In one embodiment, the electronic control circuitry 200 includes terminals, labeled with reference numbers 202, 204, 206, and 208 for connection to the first defibrillation coil electrode 40, the first pacing/sensing electrode 42, and the second defibrillation coil electrode 44 attached to the surface of the endocardial lead 24.

The electronic control circuitry 200 of the cardioverter/defibrillator 22 is encased and hermetically sealed in a housing 210 (FIGS. 1 and 5) suitable for implanting in a human body 26. In one embodiment, titanium is used for the housing 210, however, other biocompatible housing materials as are known in the art may be used. A connector block 212 (FIGS. 1 and 5) is additionally attached to the housing 210 of the cardioverter/defibrillator 22 to allow for the physical and the electrical attachment of the endocardial lead 24 and the electrodes to the cardioverter/defibrillator 22 and the encased electronic control circuitry 200.

The electronic control circuitry 200 of the cardioverter/defibrillator 22 is a programmable microprocessor-based system, with a microprocessor 214 a memory circuit 216, which contains parameters for various pacing and sensing modes, and stores data indicative of cardiac signals received by the electronic control circuitry 200. A transmitter circuit 218 is additionally coupled to the electronic control circuitry 200 and the memory circuit 214 to allow the cardioverter/defibrillator 22 to communicate with an external controller unit 220. In one embodiment, the transmitter circuit 218 and the external controller unit 220 use a wire loop antenna 222 and a radio frequency telemetric link, as is known in the art, to receive and transmit signals and data to and from the external controller unit 220 and the electronic control circuitry 200. In this manner, programming commands or instructions are transferred to the microprocessor 214 of the cardioverter/defibrillator 22 after implant, and stored cardiac data pertaining to sensed arrhythmic events within the heart 28 and subsequent therapy, or therapies, applied to correct the sensed arrhythmic event are transferred to the external controller unit 220 from the cardioverter/defibrillator 22.

In the cardioverter/defibrillator 22 of FIG. 7, the first defibrillation coil electrode 40 and the first pacing/sensing electrode 42 are coupled to a sense amplifier 224, whose output is shown connected to an R-wave detector 226. These components serve to sense and amplify the QRS waves of the heart, and apply signals indicative thereof to the microprocessor 214. Among other things, microprocessor 214 responds to the R-wave detector 226 by providing pacing signals to a pace output circuit 228, as needed according to the programmed pacing mode. Pace output circuit 228 provides output pacing signals to terminals 202 and 204, which connect to the first pacing/sensing electrode 42 and the first defibrillation coil electrode 40, for bipolar cardiac pacing. In an alternative embodiment, the pace output circuit 228 provides output pacing signals to terminal 202 and to the housing 210 of the cardioverter/defibrillator 22 to provide both unipolar sensing of the heart 28 and unipolar pacing of the heart 28.

The first defibrillation coil electrode 40 and the second defibrillation coil electrode 44 are coupled to a sense amplifier 230, whose output is connected to a cardiac morphology detector 232. These components serve to sense and amplify the QRS-waves of the cardiac cycle from the ventricular region of the heart 28, and apply signals indicative thereof to the microprocessor 214. In one embodiment, the cardiac morphology detector 232 includes an analog filter for filtering cardiac signal noise sensed by the electrodes. The cardiac signals are then A/D converted into a digital signal and subsequently received by the microprocessor 214.

Among other things, microprocessor 214 responds to the sensed QRS-waves of the cardiac cycle from the sense amplifier 230 applied to the morphology detector 232 by providing pacing signals to the pace output circuit 228, as needed according to the programmed pacing mode. Pace output circuit 228 provides output pacing signals to terminals 202 and 204, which connect to the first pacing/sensing electrode 42 and the first defibrillation electrode 40, for bipolar pacing or to the first pacing/sensing electrode 42 and the housing 210 for unipolar pacing as previously described.

The microprocessor 214 also responds to the cardiac signals sensed within the heart 28 using the endocardial lead 24 by providing signals to cardioversion/defibrillation output circuitry 234 to provide either cardioversion or defibrillation electrical energy to the heart 28 depending upon nature of the arrhythmia sensed by the cardioverter/defibrillator 22. Power to the cardioverter/defibrillator 22 is supplied by an electrochemical battery 236 that is housed within the cardioverter/defibrillator 22.

In one embodiment, the cardioversion or defibrillation electrical energy pulses delivered to the heart 28 are either a monophasic, biphasic or multiphasic pulses of electrical energy, as are known in the art. In an additional embodiment, more than one of the cardioversion or defibrillation electrical energy pulses are delivered to the heart, where the pulses are delivered either simultaneously or sequentially. In one embodiment, the defibrillation electrical energy is delivered between first defibrillation coil electrode 40 and the second defibrillation coil electrode 44 and the housing 210 of the cardioverter/defibrillator 22. In a further embodiment, the first defibrillation coil electrode 40 is a cathode terminal and the second defibrillation coil electrode 44 and the housing 210 are anode terminals. In an alternative embodiment, cardioversion or defibrillation electrical energy is delivered between the first defibrillation coil electrode 40 and the second defibrillation coil electrode 44, where, in one embodiment, the first defibrillation coil electrode 40 is a cathode terminal and the second defibrillation coil electrode 44 is an anode terminal. In another embodiment, additional defibrillation electrodes, such as subcutaneous patch electrode, epicardial defibrillation electrodes and the like can be incorporated into and added to the cardioverter/defibrillator 22 to allow for further defibrillation electrical energy pathways.

Figure 8:
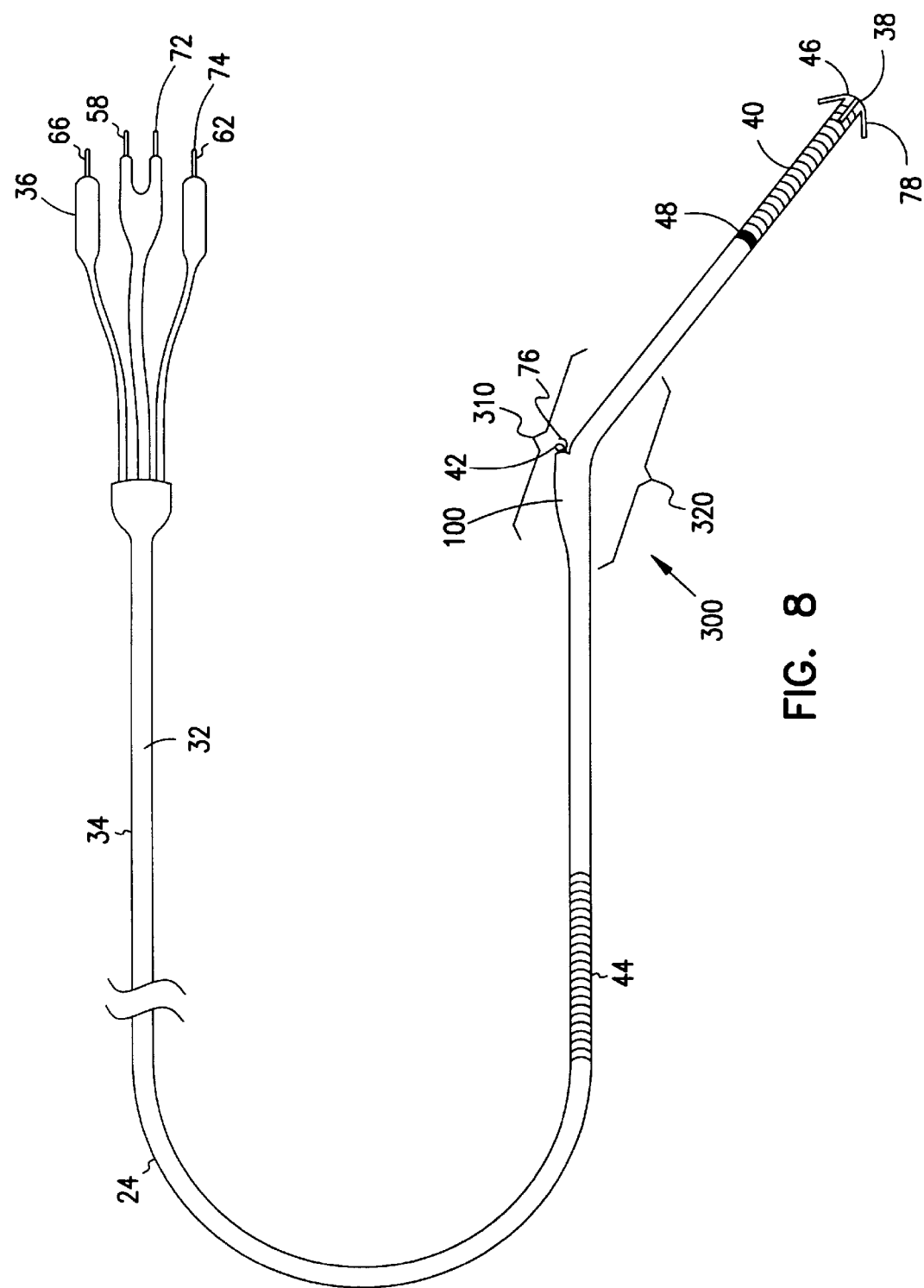
FIG. 8 is a schematic view of an embodiment of an endocardial lead according to the present invention.

Referring now to FIG. 8, there is shown an additional embodiment of an endocardial lead 24, in which the elongate body 32 of the endocardial lead 24 includes a curved portion 300. The curved portion 300 is positioned between the proximal end 36 and the distal end 38 of the elongate body 32. In one embodiment, the curved portion 300 has an outer radial surface 310 and an inner radial surface 320, where the outer radial surface 310 generally has a larger radius of curvature then the inner radial surface 320. In an additional embodiment, the electrode housing 100 is positioned generally on the outer radial surface 310 of the curved portion 300. This configuration allows the first pacing/sensing electrode 42 to extend beyond the peripheral surface 34 of the elongate body 32 along an axis that is essentially parallel with a longitudinal axis of the proximal end 36 of the elongate body 32 to engage the tissue of the heart 28. In an alternative embodiment, the first pacing/sensing electrode 42 to extend beyond the peripheral surface 34 of the elongate body 32 along an axis that has an obtuse angle (greater than 90 degrees) relative to the longitudinal axis of the proximal end 36 of the elongate body 32 to engage the tissue of the heart 28.

The curved portion 300 of the endocardial lead 24 creates an angle of between approximately 45 to 60 degrees relative to a longitudinal axis of the distal end 38 and a longitudinal axis of the proximal end 36 of the elongate body 32. In one embodiment, the curved portion 300 of the elongate body is created by a mechanical bias in one or more of the first electrical conductor 56, the second electrical conductor 60 or the third electrical conductor 64. In an additional embodiment, the polymer structure of the elongate body 32 is modified to create the curved portion 300. In one embodiment, the curved portion 300 is constructed of a polymer having an enhanced stiffness relative to the remainder of the elongate body 32. In an alternative embodiment, the curved portion 300 is molded into the elongate body 32 during the construction of the elongate body 32.

Figure 9:
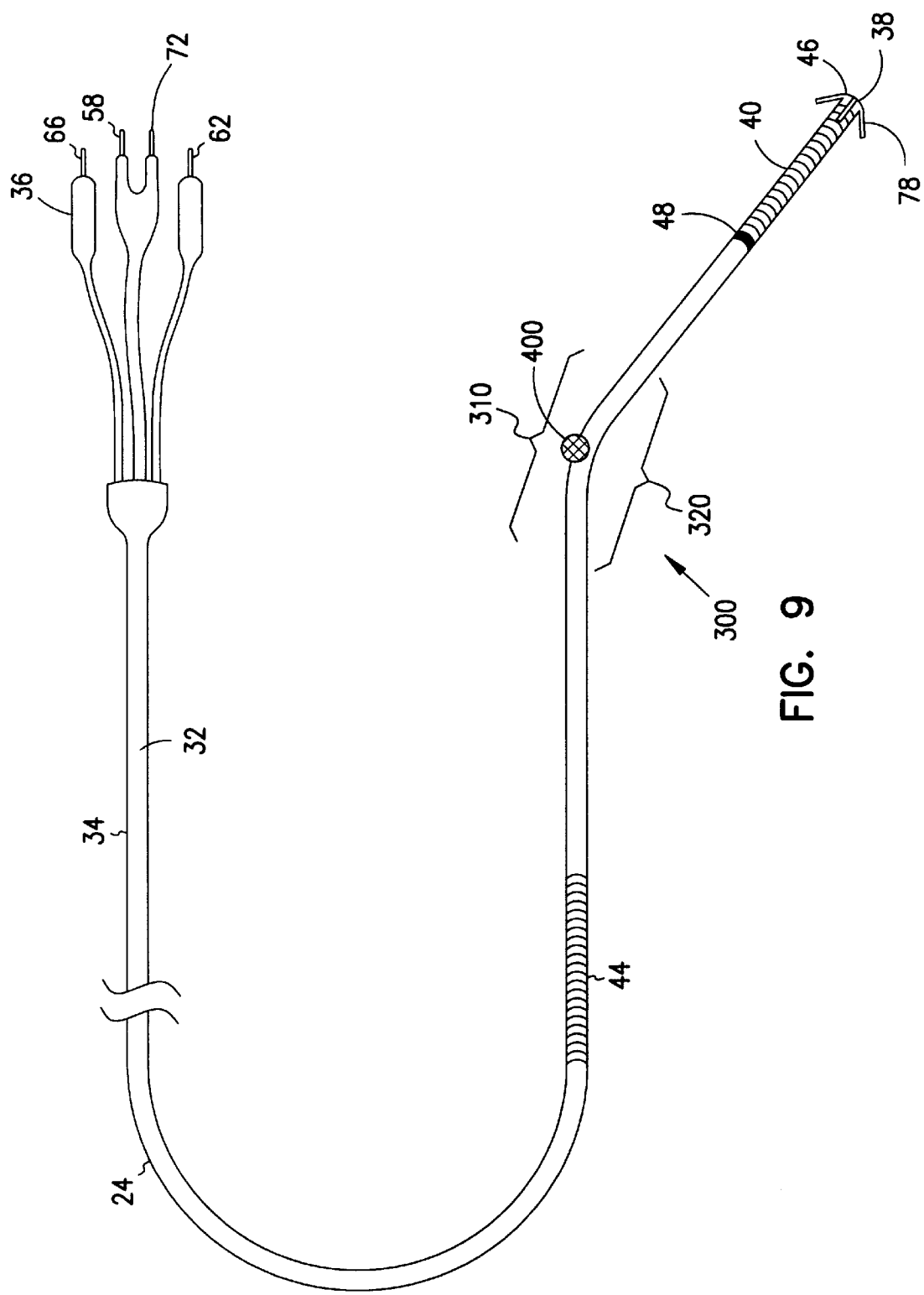
FIG. 9 is a schematic view of an embodiment of an endocardial lead according to the present invention.

Referring now to FIG. 9, there is shown an additional embodiment of the endocardial lead 24 according to the present invention. The endocardial lead 24 comprises an elongate body 32 having a peripheral surface 34, a proximal end 36 and a distal end 38. The endocardial lead 24 also includes one or more defibrillation coil electrodes and one or more pacing/sensing electrodes. In one embodiment, the endocardial lead 24 has a first defibrillation coil electrode 40, a first pacing/sensing electrode 400 and a second defibrillation coil electrode 44 attached to the peripheral surface 34 of the elongate body 32.

In one embodiment the first defibrillation coil electrode 40 and the second defibrillation coil electrode 44 are helically wound spring electrodes as are known in the art. The first defibrillation coil electrode 40 further includes a first end 46 and a second end 48, where the first end 46 is at or near the distal end 38 of the elongate body 32 and the second end 48 is spaced longitudinally along the peripheral surface from the first end 46 of the first defibrillation coil electrode 40 and the distal end 38 of the elongate body 32. In one embodiment the first end 46 of the first coil electrode 40 forms a portion of the distal end 38 of the elongate body 32. In an alternative embodiment, the first end 46 of the first coil electrode 40 is spaced longitudinally along the peripheral surface 34 from the distal end 38 by a distance in the range of 0 to 7 millimeters.

The first pacing/sensing electrode 400 is spaced longitudinally along the peripheral surface 34 from the second end 48 of the first defibrillation coil electrode 40 by a distance in the range of 1 to 10 centimeters, where an acceptable range is between 1 to 3 centimeters. In one embodiment, the spacing of the first defibrillation coil electrode 40 and the first pacing/sensing electrode 400 is to afford positioning the first defibrillation coil 40 and the first pacing/sensing electrode 400 in the right ventricle 50 of the heart 28. In one embodiment, the first defibrillation coil electrode 40 is implanted directly along the septal wall of the right ventricle 50 such that the first defibrillation coil electrode 40 is positioned longitudinally adjacent the septum of the right ventricle 50 of the heart 28 and the first pacing/sensing electrode 400 is in physical contact with a wall of the right ventricle. In one embodiment, the pacing electrode is positioned such that it is in contact with the ventricular septum of the heart. In an alternative embodiment, the first defibrillation coil electrode 40 is implanted directly along the apex location of the right ventricle 50 such that the first defibrillation coil electrode 40 is positioned longitudinally adjacent the apex location of the right ventricle 50 of the heart 28 and the first pacing/sensing electrode 400 is in physical contact with a wall of the right ventricle. In one embodiment, the pacing electrode is positioned such that it is in contact with the ventricular septum of the heart.

The second defibrillation coil electrode 44 is spaced longitudinally along the peripheral surface 34 from the first pacing/sensing electrode 400 by a distance in the range of 8 to 15 centimeters. In one embodiment, the spacing of the second defibrillation coil electrode 44 and the first defibrillation coil electrode 40 is to afford positioning the second defibrillation coil electrode 44 within a right atrial chamber 52 or a major vein leading to the right atrial chamber 52 when the first defibrillation coil electrode 40 and the first pacing/sensing electrode 400 are positioned within the right ventricle chamber 50. In one embodiment, the major vein leading to the heart right atrial chamber 52 is the superior vena cava.

FIG. 9 shows one embodiment in which the elongate body 32 of the endocardial lead 24 includes a curved portion 300. The curved portion 300 is positioned between the proximal end 36 and the distal end 38 of the elongate body 32. The curved portion 300 allow the endocardial lead 24 to be implanted within the heart 28 with the first pacing/sensing electrode 400 engaging the tissue of the heart 28 while the remaining distal portion of the endocardial lead 24, including the first defibrillation coil electrode 40, is positioned adjacent the endocardial wall of the right ventricle, where the first defibrillation coil electrode 40 is in the apex of the right ventricle.

The curved portion 300 of the endocardial lead 24 creates an angle of between approximately 45 to 60 degrees relative to a longitudinal axis of the distal end 38 and a longitudinal axis of the proximal end 36 of the elongate body 32. In one embodiment, the curved portion 300 of the elongate body is created by a mechanical bias in one or more of the first electrical conductor 56, the second electrical conductor 60 or the third electrical conductor 64. In an additional embodiment, the polymer structure of the elongate body 32 is modified to create the curved portion 300. In one embodiment, the curved portion 300 is constructed of a polymer having an enhanced stiffness relative to the remainder of the elongate body 32. In an alternative embodiment, the curved portion 300 is molded into the elongate body 32 during the construction of the elongate body 32.

In one embodiment, the curved portion 300 has an outer radial surface 310 and an inner radial surface 320, where the outer radial surface 310 generally has a larger radius of curvature then the inner radial surface 320. The first pacing/sensing electrode 400 is positioned generally on the outer radial surface 310 of the curved portion 300. This configuration allows the first pacing/sensing electrode 400 to extend beyond the peripheral surface 34 of the elongate body 32 to engage the tissue of the heart 28 when the endocardial lead 24 is positioned within the heart 28. In one embodiment, the first pacing/sensing electrode 400 and the first defibrillation coil electrode 40 are implanted within the heart such that both the first pacing/sensing electrode 400 and the first defibrillation coil electrode 40 are located within the right ventricle with the first defibrillation coil electrode 40 in the apex of the right ventricle and the first pacing/sensing electrode 400 on the ventricular septum of the heart.

In one embodiment, the first pacing/sensing electrode 400 is a porous woven mesh on the peripheral surface of the elongate body as is shown in FIG. 9. The porous woven mesh is created from implantable metal wire such as platinum/iridium alloys, titanium or other implantable metals as are known in the art. In one embodiment, the porous woven mesh has a semi-spherical shape and is positioned on the peripheral surface of the elongate body. In an alternative embodiment, the first pacing/sensing electrode is annular and encircles the peripheral surface of the elongate body. In an additional embodiment, the first pacing/sensing electrode is semi-annular and partially encircles the peripheral surface of the elongate body.

In an additional embodiment, the elongate body further has a plurality of tines 78 at or adjacent the distal end 38, the plurality of tines 78 being circumferentially spaced and projecting both radially away from the peripheral surface 34 and toward the proximal end 36 of the elongate body 32. In one embodiment, the plurality of tines is constructed of the same material used to make the elongate body 32 of the endocardial lead 24. In an alternative embodiment, the elongate body 32 of the endocardial lead 24 is physically or chemically treated to promote tissue in-growth. Tissue in-growth allows for the increased stabilization and retention of the endocardial lead 24 after being implanted in the heart 28. In one embodiment, a micro-texturing is created on the surface of the elongate body 32 from chemical or mechanical processing to allow for tissue in-growth.

Referring now to FIGS. 10 and 11, there is shown an additional embodiment of the endocardial lead 24 according to the present invention. A first electrical conductor 56 is shown extending longitudinally within the elongate body 32 from a first contact end 58 at the proximal end 36 and is electrically connected to the first defibrillation coil electrode 40. A second electrical conductor 60 is also shown extending longitudinally within the elongate body 32 from a second contact end 62 at the proximal end 36 and is electrically connected to the first pacing/sensing electrode 42. A third electrical conductor 64 is shown extending longitudinally within the elongate body 32 from a third contact end 66 at the proximal end 36 and is electrically connected to the second defibrillation coil electrode 44. Finally, a fourth electrical conductor 420 is also shown extending longitudinally within the elongate body 32 from a fourth contact end 422 at the proximal end 36 and is electrically connected to a second pacing electrode 424. In one embodiment, the first contact end 58, the second contact end 62, the third contact end 66, and the fourth contact end 422 are tubular or solid metallic pins which are constructed of titanium, stainless steel, or MP35N.

The endocardial lead 24 has at least one stylet lumen extending longitudinally in the elongate body 32. In one embodiment, the elongate body 32 has a first stylet lumen 68 and a second stylet lumen 70, where the first stylet lumen 68 extends from a first inlet end 72 at the proximal end 36 to the distal end 38. The first stylet lumen 68 is adapted to receive a guide stylet for stiffening and shaping the endocardial lead 24 during the insertion of the endocardial lead 24 into the heart 28. In one embodiment, a portion of the first stylet lumen 68 is formed by the fourth electrical conductor 420, which has an elongate helical coil configuration as is known in the art. In one embodiment, the elongate helical coil configuration extends longitudinally through the elongate body 32 to a point that is just proximal or adjacent to the second pacing electrode 424. The fourth electrical conductor 420 is then coupled to the second pacing electrode 424. The second stylet lumen 70 extends from a second inlet end 74 at the proximal end 36 to the first pacing/sensing electrode 42. The second stylet lumen 70 is formed by the second electrical conductor 60, which has an elongate helical coil configuration as is known in the art.

In an additional embodiment, the first pacing/sensing electrode 42 and the second pacing electrode 424 provide for bipolar sensing and pacing of the heart 28. In one embodiment, the second pacing electrode 424 is an annular ring electrode that extends completely around the peripheral surface 34 of the elongate body 32. In an alternative embodiment, the second pacing electrode 424 is a semi-annular ring that extends only partially around the peripheral surface 34 of the elongate body 32.

Figure 12:
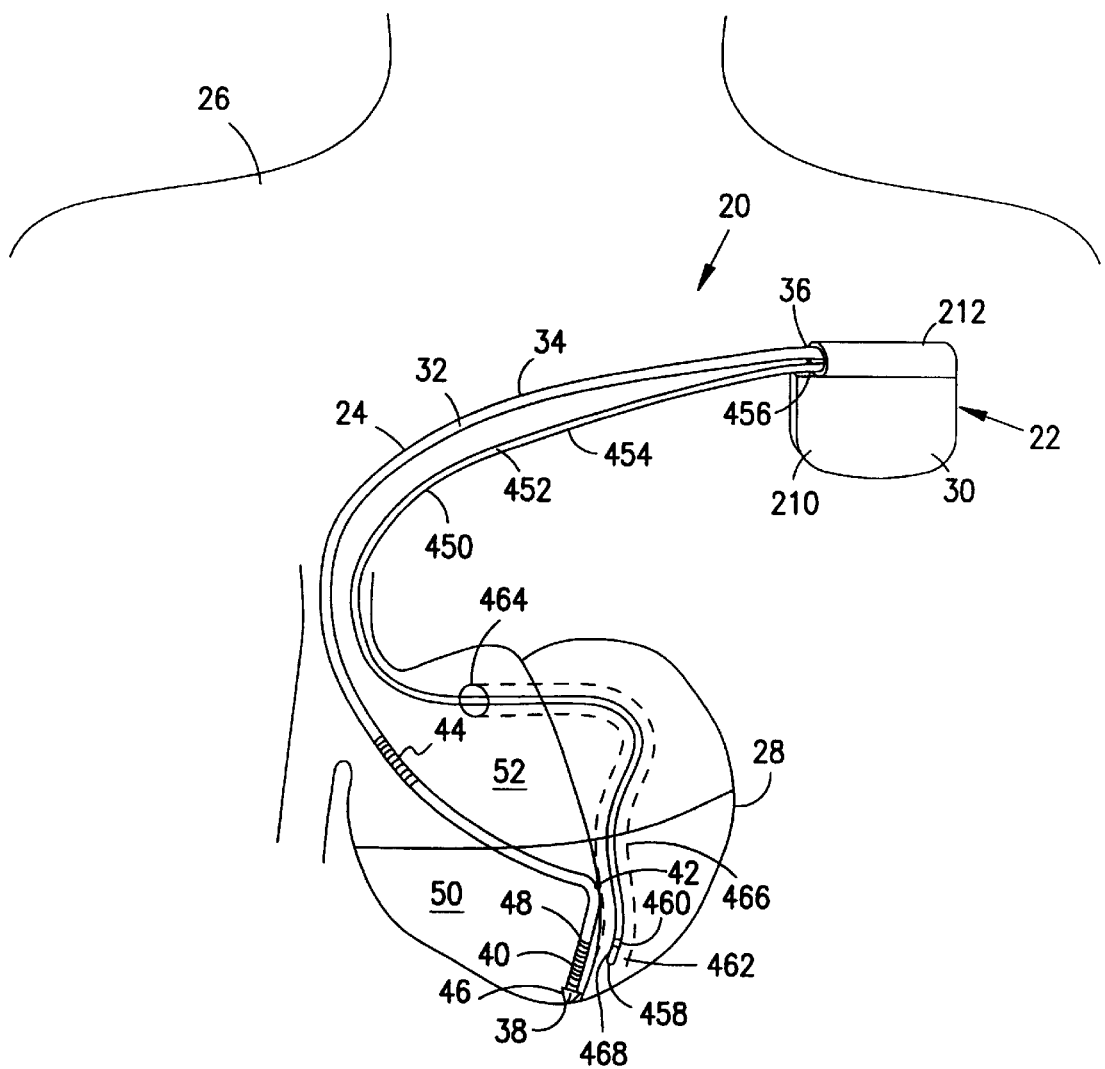
FIG. 12 is a schematic view of an implantable cardioverter/defibrillator with one embodiment of an endocardial lead implanted in a heart from which segments have been removed to show details.

Referring now to FIG. 12 of the drawings, there is shown an additional embodiment of the apparatus 20 including the cardioverter/defibrillator 22 physically and electrically coupled to the endocardial lead 24 and to a second endocardial lead 450. The apparatus 20 is implanted in the human body 26 with portions of the endocardial lead 24 and the second endocardial lead 450 inserted into the heart 28 to detect and analyze electrical cardiac signals produced by the heart 28 and to provide electrical energy to the heart 28 under certain predetermined conditions to treat ventricular arrhythmias, including ventricular tachyarrhythmias and ventricular fibrillation, of the heart 28.

The second endocardial lead 450 comprises an elongate body 452 having a peripheral surface 454, a proximal end 456 and a distal end 458. The second endocardial lead 450 also includes one or more pacing and sensing electrodes. The second endocardial lead 450 is adapted to be releasably attached to the connector block 212 to allow pacing and sensing electrodes attached to the peripheral surface of the second endocardial lead 450 to be physically and electrically coupled to the housing 210 and the electronic control circuitry 200 of the cardioverter/defibrillator 22.

In one embodiment, the second endocardial lead 450 has a distal pacing/sensing electrode 460 attached to the peripheral surface 454 of the elongate body 452. In one embodiment, the distal pacing/sensing electrode 460 is spaced longitudinally along the peripheral surface 454 from the distal end 458 of the elongate body 452 by a distance in the range of 0 to 2 centimeters, where an acceptable range is between 0 to 1 centimeters. In one embodiment, the distal pacing/sensing electrode 460 is an annular, or a semi-annular ring electrode positioned on the elongate body 452 of the second endocardial lead 450. In an alternative embodiment, the distal pacing/sensing electrode 460 is a tip electrode positioned on the distal end 458 of the second endocardial lead 450. The distal pacing/sensing electrode 460 is electrically connected to the electronic control circuitry 200 through a contact end located at the proximal end 456 which is coupled to a first distal electrode electrical conductor extending longitudinally within the elongate body 452 of the second endocardial lead 450.

In one embodiment, the second endocardial lead 450 is positioned on or adjacent a left ventricular epicardial surface 462. In one embodiment, the second endocardial lead 450 is introduced through the coronary sinus vein 464 to an apical branch of the great coronary vein 466 and advanced to a position within the great coronary vein 466, or a tributary vein to the great coronary vein 466, so that the distal pacing/sensing electrode 460 is positioned on or adjacent the left ventricular epicardial surface 462.

In one embodiment, the distal pacing/sensing electrode 460 positioned on or adjacent to the left ventricular epicardial surface 462 and the housing 210 are used to provide unipolar pacing and sensing of the ventricles of the heart. In an alternative embodiment, the distal pacing/sensing electrode 460 and the first pacing/sensing electrode 42 provide bipolar pacing and sensing of the ventricles of the heart. In an additional embodiment, a second distal pacing/sensing electrode is added to the peripheral surface of the second endocardial lead 450 to provide for bipolar sensing and pacing of the ventricles of the heart.

In an additional embodiment, the elongate body 452 further has a plurality of tines 468 at or adjacent the distal end 458, the plurality of tines 468 being circumferentially spaced and projecting both radially away from the peripheral surface 454 and toward the proximal end 456 of the elongate body 452. In one embodiment, the plurality of tines is constructed of the same material used to make the elongate body 452 of the second endocardial lead 450.

The aspects of the invention illustrated herein have been described as having applications for implantable cardioverter/defibrillators, which may include numerous pacing modes as are known in the art. However, the endocardial lead of the present invention is also used in any number of implantable or external medical devices, including external defibrillator/monitor devices. Additionally, the endocardial lead of the present invention alternatively can include additional or fewer defibrillation coil electrodes and/or pacing/sensing electrodes. For example, the endocardial lead can include only the first defibrillation coil electrode 40 and the first pacing/sensing electrode 42, where cardiac sensing is accomplished with unipolar sensing between the first pacing/sensing electrode 42 and housing 210 of the cardioverter/defibrillator 22. Additionally, unipolar defibrillation electrical energy is supplied to the heart between the first defibrillation coil electrode 40 and the housing 210 of the cardioverter/defibrillator 22.

We claim:

1. An apparatus, comprising:
   an endocardial lead, where the endocardial lead includes
      an elongate body having a proximal end and a distal end;
      a first defibrillation electrode having a first end and a second end, where the first defibrillation electrode is coupled to the elongate body with the first end at the distal end of the elongate body;
      a first pacing/sensing electrode coupled to the elongate body and spaced proximal from the second end of the first defibrillation electrode to afford positioning the first defibrillation electrode and the first pacing/sensing electrode in the right ventricle, where the first pacing/sensing electrode includes a retaining element to secure the first pacing/sensing electrode and the elongate body of the endocardial lead to the right ventricle;
      a second pacing/sensing electrode coupled to the elongate body, where the second pacing/sensing electrode is positioned proximal the first pacing/sensing electrode to afford positioning the first defibrillation electrode, the first pacing/sensing electrode and the second pacing/sensing electrode in the right ventricle;
      a second defibrillation electrode coupled to the elongate body, where the second defibrillation electrode is spaced proximal from the first pacing/sensing electrode to afford positioning the first defibrillation electrode and the first pacing/sensing electrode in the right ventricle and the second defibrillation electrode within a right atrial chamber or a major vein leading to the right atrial chamber; and
      a first conductor extending longitudinally within the elongate body from a first contact end at the proximal end to the first defibrillation electrode, a second electrical conductor extending longitudinally within the elongate body from a second contact end at the proximal end to the first pacing/sensing electrode, a third electrical conductor extends longitudinally within the elongate body from a third contact end at the proximal end to the second defibrillation electrode and a fourth electrical conductor extending longitudinally within the elongate body from a fourth contact end at the proximal end to the second pacing/sensing electrode.

2. The apparatus of claim 1, including an electrode housing having an opening, the housing adapted to sheathe the first pacing/sensing electrode and through which the first pacing/sensing electrode extends.

3. The apparatus of claim 1, where the elongate body has an arc-shaped portion, where the arc-shaped portion extends from the distal end to a predetermined point proximal the distal end and has a radius of curvature adapted to conform to a right ventricular apex, and where at least a segment of the first defibrillation electrode extends along the arc-shaped portion of the elongate body.

4. The apparatus of claim 1, where the elongate body further has a curved portion having an outer radial surface and an inner radial surface, where the outer radial surface generally has a larger radius of curvature then the inner radial surface and the first pacing/sensing electrode is positioned generally on the outer radial surface of the curved portion.

5. The apparatus of claim 4, where the curved portion creates an angle of between approximately 45 to 60 degrees relative to a longitudinal axis of the elongate body proximal the curved portion and a longitudinal axis of the elongate body distal the curved portion of the elongate body.

6. The apparatus of claim 4, where the elongate body has an arc-shaped portion, where the arc-shaped portion extends from the distal end to a predetermined point proximal the distal end and has a radius of curvature adapted to conform to a right ventricular apex, and where at least a segment of the first defibrillation electrode extends along the arc-shaped portion of the elongate body.

7. The apparatus of claim 1, where the retaining element of the first pacing/sensing electrode is a helical wire.

8. The apparatus of claim 1, where the retaining element of the first pacing/sensing electrode is a straight segment of wire having a retaining barb.

9. The apparatus of claim 1, where the first pacing/sensing electrode is a porous woven mesh.

10. The apparatus of claim 1, where the elongate body further has a curved portion having an outer radial surface and an inner radial surface, where the outer radial surface generally has a larger radius of curvature then the inner radial surface and the first pacing/sensing electrode is positioned generally on the outer radial surface of the curved portion.

11. The apparatus of claim 10, where the curved portion creates an angle of between approximately 45 to 60 degrees relative to a longitudinal axis of the elongate body proximal the curved portion and a longitudinal axis of the elongate body distal the curved portion of the elongate body.

12. The apparatus of claim 10, where the elongate body has an arc-shaped portion, where the arc-shaped portion extends from the distal end to a predetermined point proximal the distal end and has a radius of curvature adapted to conform to an apex of a right ventricle, and where at least a segment of the first defibrillation electrode extends along the arc-shaped portion of the elongate body.

13. The apparatus of claim 1, including an implantable housing,
    electronic control circuitry within the implantable housing, where the endocardial lead is coupled to the implantable housing and the electronic control circuitry, where the electronic control circuitry receives cardiac signals through both the first defibrillation electrode and the first pacing/sensing electrode, and the electronic control circuitry, upon detecting a ventricular arrhythmia, delivers a defibrillation pulse through the first defibrillation electrode.

14. The apparatus of claim 13, including a second endocardial lead having a distal pacing/sensing electrode, where the second endocardial lead is adapted to be implanted into the great coronary vein to position the distal pacing/sensing electrode adjacent the left ventricular epicardial surface, and where the second lead and the distal pacing/sensing electrode are attached to the implantable housing and the electronic control circuitry to allow for a cardiac signal to be sensed through the distal pacing/sensing electrode.

15. The apparatus of claim 14, where the cardiac signal is a bipolar cardiac signal sensed between the first pacing/sensing electrode of the first endocardial lead and the distal pacing/sensing electrode of the second endocardial lead.

16. A method, comprising:
    providing an endocardial lead having a first defibrillation coil located at the distal end of the endocardial lead, and a first pacing/sensing electrode spaced proximally from the first defibrillation coil electrode;

providing a second endocardial lead having at least a first distal pacing electrode at or near the distal end; and positioning the first defibrillation coil and the first pacing/sensing electrode within a right ventricle and the first distal pacing electrode of the second endocardial lead within the great coronary vein with the first distal pacing electrode positioned on or adjacent a left ventricular epicardial surface.

17. The method of claim 16, including:

positioning the first defibrillation coil longitudinally adjacent a septal location of the right ventricle; and positioning the first pacing/sensing electrode on a septal wall of the right ventricle of the heart.

18. The method of claim 16, including:

positioning the first defibrillation coil in an apex of the right ventricle; and positioning the first pacing/sensing electrode on a septal wall of the right ventricle of the heart.

19. The method of claim 16, including:

positioning the first defibrillation coil longitudinally adjacent a septal location of the right ventricle; and positioning the first pacing/sensing electrode on a septal wall of the right ventricle of the heart.

20. The method of claim 16, including:

positioning the first defibrillation coil in an apex of the right ventricle; and positioning the first pacing/sensing electrode on a septal wall of the right ventricle of the heart.

21. An apparatus, comprising:

an endocardial lead, where the endocardial lead includes
an elongate body having a proximal end, a distal end and an arc-shaped portion, where the arc-shaped portion extends from the distal end to a predetermined point proximal the distal end and has a radius of curvature adapted to conform to a right ventricular apex;

a first defibrillation electrode having a first end and a second end, where the first defibrillation electrode is coupled to the elongate body with the first end at the distal end of the elongate body, and where at least a segment of the first defibrillation electrode extends along the arc-shaped portion of the elongate body;

a first pacing/sensing electrode coupled to the elongate body and spaced proximal from the second end of the first defibrillation electrode to afford positioning the first defibrillation electrode and the first pacing/sensing electrode in the right ventricle, where the first pacing/sensing electrode includes a retaining element to secure the first pacing/sensing electrode and the elongate body of the endocardial lead to the right ventricle;

a second defibrillation electrode coupled to the elongate body, where the second defibrillation electrode is spaced proximal from the first pacing/sensing electrode to afford positioning the first defibrillation electrode and the first pacing/sensing electrode in the right ventricle and the second defibrillation electrode within a right atrial chamber or a major vein leading to the right atrial chamber; and a first conductor extending longitudinally within the elongate body from a first contact end at the proximal end to the first defibrillation electrode, a second electrical conductor extending longitudinally within the elongate body from a second contact end at the proximal end to the first pacing/sensing electrode, and a third electrical conductor extends longitudinally within the elongate body from a third contact end at the proximal end to the second defibrillation electrode.

22. The apparatus of claim 21, including an electrode housing having an opening, the housing adapted to sheathe the first pacing/sensing electrode and through which the first pacing/sensing electrode extends.

23. The apparatus of claim 21, where the elongate body further includes a second pacing/sensing electrode coupled to the elongate body, where the second pacing/sensing electrode is positioned proximal the first pacing/sensing electrode to afford positioning the first defibrillation electrode, the first pacing/sensing electrode and the second pacing/sensing electrode in the right ventricle; and a fourth electrical conductor extending longitudinally within the elongate body from a fourth contact end at the proximal end to the second pacing/sensing electrode.

24. The apparatus of claim 21, where the elongate body further has a curved portion having an outer radial surface and an inner radial surface, where the outer radial surface generally has a larger radius of curvature then the inner radial surface and the first pacing/sensing electrode is positioned generally on the outer radial surface of the curved portion.

25. The apparatus of claim 21, where the curved portion creates an angle of between approximately 45 to 60 degrees relative to a longitudinal axis of the elongate body proximal the curved portion and a longitudinal axis of the elongate body distal the curved portion of the elongate body.

26. The apparatus of claim 21, where the retaining element of the first pacing/sensing electrode is a helical wire.

27. The apparatus of claim 21, where the retaining element of the first pacing/sensing electrode is a straight segment of wire having a retaining barb.

28. The apparatus of claim 21, where the first pacing/sensing electrode is a porous woven mesh.

29. The apparatus of claim 21, including an implantable housing, electronic control circuitry within the implantable housing, where the endocardial lead is coupled to the implantable housing and the electronic control circuitry, where the electronic control circuitry receives cardiac signals through both the first defibrillation electrode and the first pacing/sensing electrode, and the electronic control circuitry, upon detecting a ventricular arrhythmia, delivers a defibrillation pulse through the first defibrillation electrode.

30. The apparatus of claim 29, including a second endocardial lead having a distal pacing/sensing electrode, where the second endocardial lead is adapted to be implanted into the great coronary vein to position the distal pacing/sensing electrode adjacent the left ventricular epicardial surface, and where the second lead and the distal pacing/sensing electrode are attached to the implantable housing and the electronic control circuitry to allow for a cardiac signal to be sensed through the distal pacing/sensing electrode.

31. The apparatus of claim 30, where the cardiac signal is a bipolar cardiac signal sensed between the first pacing/sensing electrode of the first endocardial lead and the distal pacing/sensing electrode of the second endocardial lead.

32. An apparatus, comprising:

an endocardial lead, where the endocardial lead includes
an elongate body having a proximal end, a distal end, an arc-shaped portion, where the arc-shaped portion extends from the distal end to a predetermined point proximal the distal end and has a radius of curvature adapted to conform to an apex of a right ventricle, and a curved portion having an outer radial surface and an inner radial surface, where the outer radial surface generally has a larger radius of curvature then the inner radial surface;

a first defibrillation electrode having a first end and a second end, where the first defibrillation electrode is coupled to the elongate body with the first end at the distal end of the elongate body, and where at least a segment of the first defibrillation electrode extends along the arc-shaped portion of the elongate body;

a first pacing/sensing electrode coupled to the elongate body, positioned generally on the outer radial surface of the curved portion of the elongate body and spaced proximal from the second end of the first defibrillation electrode to afford positioning the first defibrillation electrode and the first pacing/sensing electrode in the right ventricle; and a first conductor extending longitudinally within the elongate body from a first contact end at the proximal end to the first defibrillation electrode, and a second electrical conductor extending longitudinally within the elongate body from a second contact end at the proximal end to the first pacing/sensing electrode.

33. The apparatus of claim 32, where the curved portion creates an angle of between approximately 45 to 60 degrees relative to a longitudinal axis of the elongate body proximal the curved portion and a longitudinal axis of the elongate body distal the curved portion of the elongate body.

34. The apparatus of claim 32, including an electrode housing having an opening, the housing adapted to sheathe the first pacing/sensing electrode and through which the first pacing/sensing electrode extends.

35. The apparatus of claim 32, further including a second defibrillation electrode coupled to the elongate body, where the second defibrillation electrode is spaced proximal from the first pacing/sensing electrode to afford positioning the first defibrillation electrode and the first pacing/sensing electrode in the right ventricle and the second defibrillation electrode within a right atrial chamber or a major vein leading to the right atrial chamber; and a third electrical conductor extends longitudinally within the elongate body from a third contact end at the proximal end to the second defibrillation electrode.

36. The apparatus of claim 32, where the elongate body further includes a second pacing/sensing electrode coupled to the elongate body, where the second pacing/sensing electrode is positioned proximal the first pacing/sensing electrode to afford positioning the first defibrillation electrode, the first pacing/sensing electrode and the second pacing/sensing electrode in the right ventricle; and a fourth electrical conductor extending longitudinally within the elongate body from a fourth contact end at the proximal end to the second pacing/sensing electrode.

37. The apparatus of claim 32, where the first pacing/sensing electrode further includes a retaining element to secure the first pacing/sensing electrode and the elongate body of the endocardial lead to the right ventricle.

38. The apparatus of claim 37, where the retaining element of the first pacing/sensing electrode is a helical wire.

39. The apparatus of claim 37, where the retaining element of the first pacing/sensing electrode is a straight segment of wire having a retaining barb.

40. The apparatus of claim 32, where the first pacing/sensing electrode is a porous woven mesh.

41. The apparatus of claim 32, including an implantable housing, electronic control circuitry within the implantable housing, where the endocardial lead is coupled to the implantable housing and the electronic control circuitry, where the electronic control circuitry receives cardiac signals through both the first defibrillation electrode and the first pacing/sensing electrode, and the electronic control circuitry, upon detecting a ventricular arrhythmia, delivers a defibrillation pulse through the first defibrillation electrode.

42. The apparatus of claim 41, including a second endocardial lead having a distal pacing/sensing electrode, where the second endocardial lead is adapted to be implanted into the great coronary vein to position the distal pacing/sensing electrode adjacent the left ventricular epicardial surface, and where the second lead and the distal pacing/sensing electrode are attached to the implantable housing and the electronic control circuitry to allow for a cardiac signal to be sensed through the distal pacing/sensing electrode.

43. The apparatus of claim 42, where the cardiac signal is a bipolar cardiac signal sensed between the first pacing/sensing electrode of the first endocardial lead and the distal pacing/sensing electrode of the second endocardial lead.

44. An apparatus, comprising:

an endocardial lead, where the endocardial lead includes an elongate body having a proximal end and a distal end;

a first defibrillation electrode having a first end and a second end, where the first defibrillation electrode is coupled to the elongate body with the first end at the distal end of the elongate body;

a first pacing/sensing electrode coupled to the elongate body and spaced proximal from the second end of the first defibrillation electrode to afford positioning the first defibrillation electrode and the first pacing/sensing electrode in the right ventricle;

a first conductor extending longitudinally within the elongate body from a first contact end at the proximal end to the first defibrillation electrode, and a second electrical conductor extending longitudinally within the elongate body from a second contact end at the proximal end to the first pacing/sensing electrode;

a second endocardial lead, where the second endocardial lead is adapted to be implanted into the great coronary vein to position a distal pacing/sensing electrode adjacent the left ventricular epicardial surface;

an implantable housing; and electronic control circuitry within the implantable housing, where the endocardial lead and the second endocardial lead are coupled to the implantable housing and the electronic control circuitry, where the electronic control circuitry receives cardiac signals through both the first defibrillation electrode and the first pacing/sensing electrode of the endocardial lead and the distal pacing/sensing electrode of the second endocardial lead, and the electronic control circuitry, upon detecting a ventricular arrhythmia from the cardiac signals, delivers a defibrillation pulse through the first defibrillation electrode.

45. The apparatus of claim 44, where the first pacing/sensing electrode further includes a retaining element to secure the first pacing/sensing electrode and the elongate body of the endocardial lead to the right ventricle.

46. The apparatus of claim 45, including an electrode housing having an opening, the housing adapted to sheathe the first pacing/sensing electrode and through which the first pacing/sensing electrode extends.

47. The apparatus of claim 45, further including a second defibrillation electrode coupled to the elongate body, where the second defibrillation electrode is spaced proximal from the first pacing/sensing electrode to afford positioning the first defibrillation electrode and the first pacing/sensing electrode in the right ventricle and the second defibrillation electrode within a right atrial chamber or a major vein leading to the right atrial chamber; and a third electrical conductor extends longitudinally within the elongate body from a third contact end at the proximal end to the second defibrillation electrode.

48. The apparatus of claim 47, where the elongate body has an arc-shaped portion, where the arc-shaped portion extends from the distal end to a predetermined point proximal the distal end and has a radius of curvature adapted to conform to a right ventricular apex, and where at least a segment of the first defibrillation electrode extends along the arc-shaped portion of the elongate body.

49. The apparatus of claim 47, where the elongate body further includes a second pacing/sensing electrode coupled to the elongate body, where the second pacing/sensing electrode is positioned proximal the first pacing/sensing electrode to afford positioning the first defibrillation electrode, the first pacing/sensing electrode and the second pacing/sensing electrode in the right ventricle; and a fourth electrical conductor extending longitudinally within the elongate body from a fourth contact end at the proximal end to the second pacing/sensing electrode.

50. The apparatus of claim 47, where the elongate body further has a curved portion having an outer radial surface and an inner radial surface, where the outer radial surface generally has a larger radius of curvature then the inner radial surface and the first pacing/sensing electrode is positioned generally on the outer radial surface of the curved portion.

51. The apparatus of claim 50, where the curved portion creates an angle of between approximately 45 to 60 degrees relative to a longitudinal axis of the elongate body proximal the curved portion and a longitudinal axis of the elongate body distal the curved portion of the elongate body.

52. The apparatus of claim 50, where the elongate body has an arc-shaped portion, where the arc-shaped portion extends from the distal end to a predetermined point proximal the distal end and has a radius of curvature adapted to conform to a right ventricular apex, and where at least a segment of the first defibrillation electrode extends along the arc-shaped portion of the elongate body.

53. The apparatus of claim 45, where the retaining element of the first pacing/sensing electrode is a helical wire.

54. The apparatus of claim 45, where the retaining element of the first pacing/sensing electrode is a straight segment of wire having a retaining barb.

55. The apparatus of claim 45, where the first pacing/sensing electrode is a porous woven mesh.

56. The apparatus of claim 44, where the elongate body further has a curved portion having an outer radial surface and an inner radial surface, where the outer radial surface generally has a larger radius of curvature then the inner radial surface and the first pacing/sensing electrode is positioned generally on the outer radial surface of the curved portion.

57. The apparatus of claim 56, where the curved portion creates an angle of between approximately 45 to 60 degrees relative to a longitudinal axis of the elongate body proximal the curved portion and a longitudinal axis of the elongate body distal the curved portion of the elongate body.

58. The apparatus of claim 56, where the elongate body has an arc-shaped portion, where the arc-shaped portion extends from the distal end to a predetermined point proximal the distal end and has a radius of curvature adapted to conform to an apex of a right ventricle, and where at least a segment of the first defibrillation electrode extends along the arc-shaped portion of the elongate body.

59. The apparatus of claim 44, where the cardiac signal is a bipolar cardiac signal sensed between the first pacing/sensing electrode of the first endocardial lead and the distal pacing/sensing electrode of the second endocardial lead.

* * * * *

UNITED STATES PATENT AND TRADEMARK OFFICE
CERTIFICATE OF CORRECTION

PATENT NO. : 6,256,541 B1
DATED : July 3, 2001
INVENTOR(S) : John E. Heil, Ronald W. Heil Jr., Avram Scheiner, Yayun Lin, Lyle A. Bye, J. John Lattuca It is certified that error appears in the above-identified patent and that said Letters Patent is hereby corrected as shown below:

<u>Title page, item [54], column 1, lines 1-3,</u>
delete "ENDOCARDIAL LEAD HAVING DEFIBRILLATION AND SENSING ELECTRODES WITH SEPTAL ANCHORING" and insert -- ENDOCARDIAL LEAD HAVING DEFIBRILLATING AND SENSING/PACING ELECTRODES --, therefor.

Item [75], under "Inventors", delete "White Bear Lake" and insert -- North Oaks --, therefor.

Signed and Sealed this

Twenty-fifth Day of December, 2001

Attest:

*Attesting Officer*

JAMES E. ROGAN
*Director of the United States Patent and Trademark Office*